(12) United States Patent
Fang et al.

(10) Patent No.: US 11,746,322 B2
(45) Date of Patent: Sep. 5, 2023

(54) PROTEINASE-FREE COATINGS FOR COLONY PASSAGING

(71) Applicant: CORNING INCORPORATED, Corning, NY (US)

(72) Inventors: Ye Fang, Painted Post, NY (US); Ann MeeJin Ferrie, Painted Post, NY (US); Vasiliy Nikolaevich Goral, Painted Post, NY (US); David Henry, Fontaine le Port (FR); Martial Hervy, Veneux les sablons (FR); Corinne Walerack, Veneux les sablons (FR); Yue Zhou, Horseheads, NY (US)

(73) Assignee: CORNING INCORPORATED, Corning, NY (US)

( * ) Notice: Subject to any disclaimer, the term of this patent is extended or adjusted under 35 U.S.C. 154(b) by 146 days.

(21) Appl. No.: 17/022,764

(22) Filed: Sep. 16, 2020

(65) Prior Publication Data
US 2021/0062142 A1 Mar. 4, 2021

Related U.S. Application Data

(62) Division of application No. 15/537,111, filed as application No. PCT/US2015/065957 on Dec. 16, 2015, now Pat. No. 10,808,221.

(60) Provisional application No. 62/095,147, filed on Dec. 22, 2014.

(51) Int. Cl.
*C12N 5/00* (2006.01)
*C08J 3/24* (2006.01)
*C09D 167/00* (2006.01)

(52) U.S. Cl.
CPC ............ *C12N 5/0075* (2013.01); *C08J 3/24* (2013.01); *C09D 167/00* (2013.01); *C12N 5/0068* (2013.01); *C12N 2533/32* (2013.01); *C12N 2533/40* (2013.01); *C12N 2533/50* (2013.01); *C12N 2533/74* (2013.01); *C12N 2537/10* (2013.01)

(58) Field of Classification Search
CPC ............ C12N 5/0075; C12N 5/0068; C12N 2533/32; C12N 2533/40; C12N 2533/50; C12N 2533/74; C12N 2537/10; C08J 3/24; C09D 167/00
See application file for complete search history.

(56) References Cited

U.S. PATENT DOCUMENTS

| | | | |
|---|---|---|---|
| 6,821,107 | B1 | 11/2004 | Hara et al. |
| 8,557,583 | B2 | 10/2013 | Watanabe et al. |
| 2008/0227203 | A1 | 9/2008 | Watanabe et al. |
| 2010/0087002 | A1 | 4/2010 | Fryer |
| 2011/0027890 | A1 | 2/2011 | Fujita et al. |
| 2012/0156779 | A1 | 6/2012 | Anneren et al. |
| 2012/0220035 | A1 | 8/2012 | Lu et al. |
| 2012/0309089 | A1 | 12/2012 | Tseng et al. |
| 2013/0323841 | A1 | 12/2013 | Kruglick |
| 2014/0011960 | A1 | 1/2014 | Konno et al. |
| 2014/0186941 | A1 | 7/2014 | Zhou et al. |
| 2014/0295553 | A1 | 10/2014 | Du et al. |
| 2016/0145567 | A1 | 5/2016 | Henry et al. |

FOREIGN PATENT DOCUMENTS

| | | |
|---|---|---|
| DE | 19707910 A1 | 9/1998 |
| WO | 2012/009363 A1 | 1/2012 |
| WO | 2012/158235 A2 | 11/2012 |
| WO | 2014/209865 A1 | 12/2014 |

OTHER PUBLICATIONS

Lee KY, Mooney DJ. Alginate: properties and biomedical applications. Prog Polym Sci. Jan. 2012;37(1):106-126. doi: 10.1016/j.progpolymsci.2011.06.003. PMID: 22125349; PMCID: PMC3223967.*
Jiaxi Cui, Miao Wang, Yijun Zheng, Gemma Maria Rodríguez Muñiz, and Aránzazu del Campo Biomacromolecules, 2013 14 (5), 1251-1256, DOI: 10.1021/bm400022h.*
Barralet JE, Wang L, Lawson M, Triffitt JT, Cooper PR, Shelton RM. Comparison of bone marrow cell growth on 2D and 3D alginate hydrogels. J Mater Sci Mater Med. Jun. 2005;16(6):515-9. doi: 10.1007/s10856-005-0526-z. PMID: 15928866.*
Britannica Online Encyclopedia,definition of Surface, retrieved on Oct. 1, 2019, 1 page.
Da Silva et al., Carbohydrate Polymers, 2009, vol. 77, p. 736-742.
International Search Report and Written Opinion of the International Searching Authority; PCT/US2015/065957; dated Mar. 1, 2016; 13 Pages; European Patent Office.
Kuo et al., Biomaterials, 2001, 22, p. 511-521.
Machida-Sano, I. et al., "A novel harvesting method for cultured cells using iron-cross-linked alginate films as culture substrates." Biotechnology Applied Biochemistry, vol. 55, Issue 1, pp. 1-8, Jan. 2010.
Molecular Mass of RGD, retrieved from Google on Oct. 3, 2019, 1 page.
Picart et al., Advanced Functional Materials, 2005, No. 1, p. 83-94.
Terazono, H. et al., "A non-destructive culturing and cell sorting method for caromyocytes and neurons using a double alginate layer." PLOS One, vol. 7, Issue 8, e42485, pp. 1-7, Aug. 3, 2012.
Zhang, R. et al., "A thermoresponsive and chemically defined hydrogel for long-term-culture of human embryonic stem cells." Nature Communications, vol. 4, Article No. 1335, pp. 1-10, Jan. 8, 2013.

* cited by examiner

*Primary Examiner* — Kade Ariani
(74) *Attorney, Agent, or Firm* — Chandra J. Duncan

(57) ABSTRACT

A cell culture article includes a substrate having a polymer coating that is conducive to colony passaging of cells cultured on the coating. Example polymer coatings are formed from polygalacturonic acid (PGA), alginate, or combinations thereof. Cells cultured on the polymer coating can be separated from the substrate as a colony or layer of cells by exposing the polymer coating to (i) a chelating agent, (ii) a proteinase-free enzyme, or (iii) a chelating agent and a proteinase-free enzyme.

6 Claims, 29 Drawing Sheets

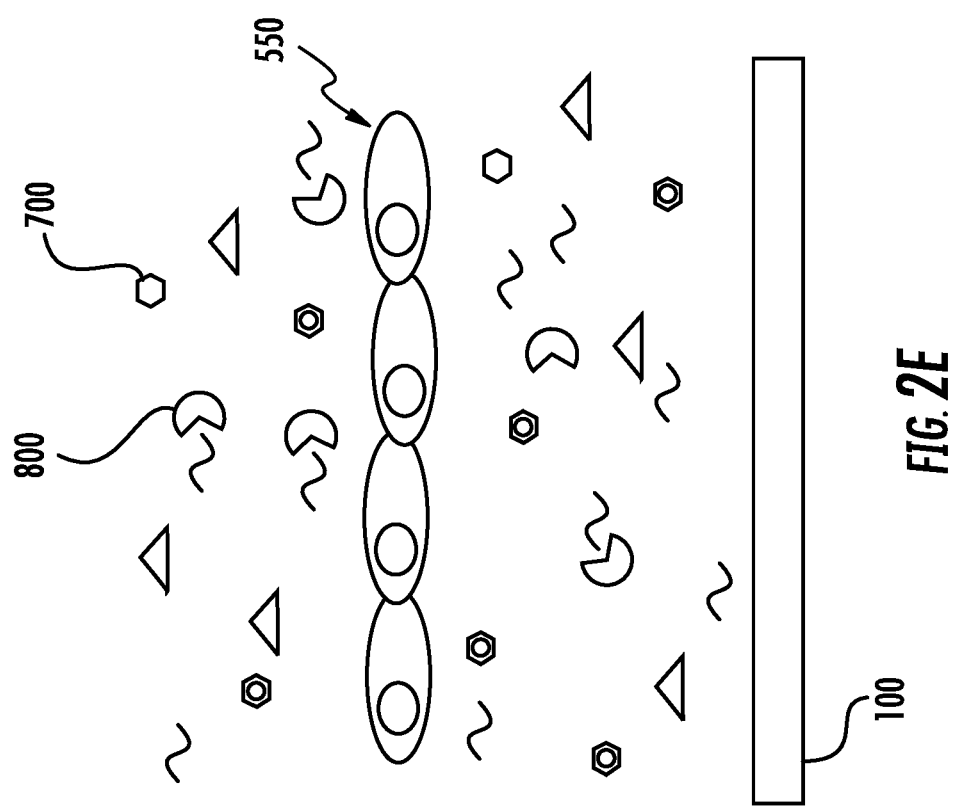

PROTEINASE-FREE COATINGS FOR COLONY PASSAGING

This application claims the benefit of priority under 35 U.S.C. § 119 of U.S. Provisional Application Ser. No. 62/095147 filed on Dec. 22, 2014 the content of which is relied upon and incorporated herein by reference in its entirety.

BACKGROUND

Field

The present disclosure relates generally to articles and methods for cell dissociation, and more specifically to polymer-coated substrates and related protocols for colony passaging of human stem cells.

Technical Background

Stem cell research is a rapidly advancing field with the potential to develop therapeutic agents to treat diseases as well as study disease development. The culture of human stem cells shares many of the same protocols as standard mammalian cell culture. However, the successful culture and maintenance of human stem cells, including induced pluripotent stem cells (IPSCs) and human embryonic stem cells (hESCs) in an undifferentiated state requires additional considerations to ensure that cells maintain their key characteristics of self-renewal and pluripotency.

Successful stem cell culture benefits from the re-creation of an in vivo stem cell microenvironment, which includes growth factors, cell-to-cell interactions, and cell-to-matrix adhesions. Unlike many cell types, human stem cells are grown in aggregates, or colonies, which helps create this microenvironment.

Conventional culture of human stem cells involves exposure to media enriched with growth factors found in fetal bovine serum (FBS) or defined serum replacements, for example. Further, such human stem cell culture systems may utilize support cells such as an inactivated mouse embryonic fibroblast (MEF) feeder layer to support growth and prevent differentiation. These cells provide intercellular interactions, extracellular scaffolding, and factors creating a robust and stable cell culture environment.

There are several fundamental aspects involved in the culturing of cells, including thawing frozen stocks, plating cells in culture vessels, changing media, passaging and cryopreservation. Passaging refers to the removal of cells from one culture vessel and their subsequent transfer to one or more new culture vessels. Passaging is advantageous in minimizing the harmful effects of overcrowding and for promoting expansion of the culture.

Traditional proteinase-based methods for harvesting cells typically produce only single cells and may also adversely affect viability and stem character of those cells produced. During dissociation, the cells are removed from a growth surface by scraping such as with a cell scraper or lifter. However, this process is labor intensive and results in cells having an unacceptably high degree of variability (e.g., colony size, viability, etc.). Moreover, the use of a scraper is not suitable for high density cell culture formats such as multi-layer culture vessels, roller bottles, or microcarriers.

In view of the foregoing, improved methods and apparatus for colony passaging of stem cells would be beneficial.

BRIEF SUMMARY

In accordance with embodiments of the present disclosure, a substrate for culturing cells comprises a polymer coating disposed on a surface of the substrate. The polymer coating is cross-linked or grafted to the substrate and comprises at least one of PGA and alginate. The polymer coating may be cross-linked with calcium ions.

A method for culturing cells comprises forming a polymer coating on a substrate surface, wherein the polymer coating comprises at least one of PGA and alginate, forming a cell adhesion layer on the polymer coating, culturing cells on the cell adhesion layer, and separating the cells from the cell adhesion layer as a colony or layer of cells by exposing the polymer coating to (i) a chelating agent, (ii) a proteinase-free enzyme, or (iii) a chelating agent and a proteinase-free enzyme.

Additional features and advantages of the subject matter of the present disclosure will be set forth in the detailed description which follows, and in part will be readily apparent to those skilled in the art from that description or recognized by practicing the subject matter of the present disclosure as described herein, including the detailed description which follows, the claims, as well as the appended drawings.

It is to be understood that both the foregoing general description and the following detailed description present embodiments of the subject matter of the present disclosure, and are intended to provide an overview or framework for understanding the nature and character of the subject matter of the present disclosure as it is claimed. The accompanying drawings are included to provide a further understanding of the subject matter of the present disclosure, and are incorporated into and constitute a part of this specification. The drawings illustrate various embodiments of the subject matter of the present disclosure and together with the description serve to explain the principles and operations of the subject matter of the present disclosure. Additionally, the drawings and descriptions are meant to be merely illustrative, and are not intended to limit the scope of the claims in any manner.

BRIEF DESCRIPTION OF THE DRAWINGS

The following detailed description of specific embodiments of the present disclosure can be best understood when read in conjunction with the following drawings, where like structure is indicated with like reference numerals and in which:

FIG. 2E is a schematic diagram of the polymer-coated substrate in a step of harvesting cells from the substrate according to one embodiment;

DETAILED DESCRIPTION

Figure 1A:
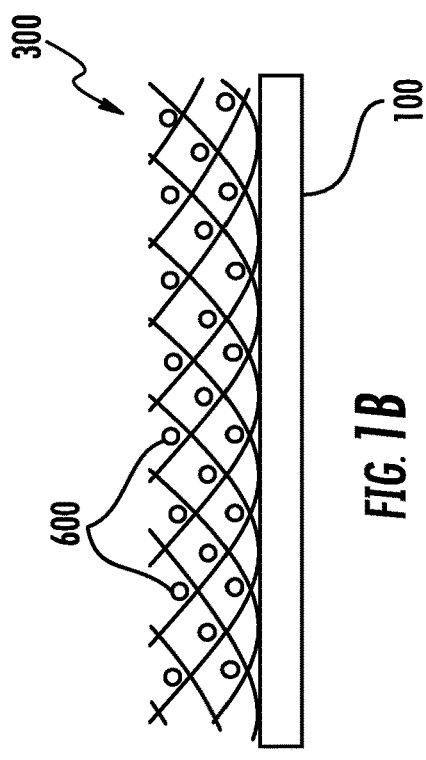
FIG. 1A is a schematic diagram of a polymer-coated substrate and its method of use according to one embodiment.

Reference will now be made in greater detail to various embodiments of the subject matter of the present disclosure, some embodiments of which are illustrated in the accompanying drawings. The same reference numerals will be used throughout the drawings to refer to the same or similar parts.

Disclosed is a cell culture article that comprises a polymer coating conducive to colony passaging of cells cultured on the coating. Exemplary cells include embryonic stem cells and pluripotent stem cells, including human embryonic stem cells (hESCs) and induced pluripotent stem cells (IPSCs), as well as other cell types that are beneficially passaged as colonies or clusters. Colony passaging is a favored approach for preserving cell-to-cell associations that are important for promoting, inter alia, cell self-renewal and genetic stability. Cells may be cultured directly on the polymer coating or on an intervening layer provided between the cells and the polymer coating.

During cell harvesting, the polymer coating may be rendered un-cross-linked or at least partially digested, e.g., by a proteinase-free enzyme, to release the cells without damaging the cell-to-cell interactions within the colony or cell layer.

Example polymer coatings comprise polygalacturonic acid (PGA), alginate, and combinations thereof. Polygalacturonic acid, if used, may be cross-linked or partially cross-linked such as with calcium.

The polymer layer may be provided on a substrate. The substrate may be any suitable support or vessel such as microcarriers, Petri dishes, bottles, beakers, flasks, and multi-layer vessels such as CellSTACK® culture chambers or HYPERflask® cell culture vessels. Because the polymer layer (as well as any cell adhesion layer) can be applied to wide variety of substrate geometries, the disclosed apparatus enables colony dependent cell culture that is readily scalable in connection with protocols where manual scraping would not be possible.

One or more cell adhesion layers may be disposed at least partially over the polymer layer in order to provide a cell-facing adhesion layer. The cell adhesion layer(s), if provided, may comprise an intervening layer formed over the polymer coating, or may be integrated within the polymer coating such as by forming a polymer coating/adhesion layer mixture or co-polymer. The adhesion layer may be grafted (or covalently-bonded) to the polymer coating. Example cell adhesion layers comprise extracellular matrix (ECM) proteins, such as laminin, collagen or fibronectin, or synthetic molecules such as poly-D-lysine or a Synthemax® surface, which promote cell attachment and growth. The cell adhesion layer(s) promote cell attachment and growth.

The architecture of example polymer-coated substrates is illustrated in FIGS. 1 and 2 in connection with their associated methods of use according to various embodiments. In one embodiment, the polymer coating is grafted onto a substrate. The polymer chains may be grafted to the substrate at one or more sites along the polymer chain.

Figure 3A:
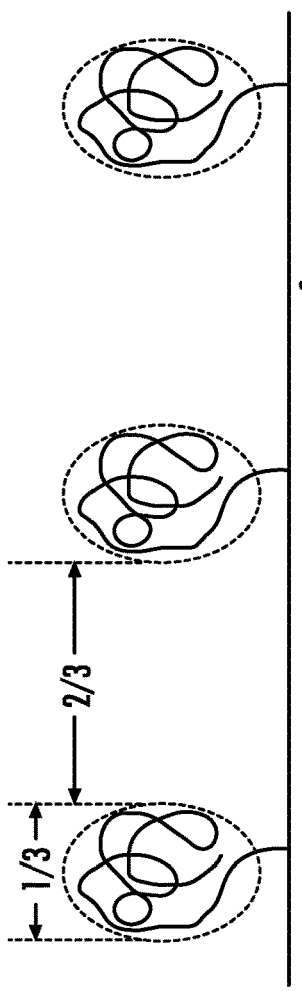
FIG. 3A is a schematic showing hypothetical cases of grafted polymers on a flat substrate in a brush configuration according to an embodiment.
Figure 3B:
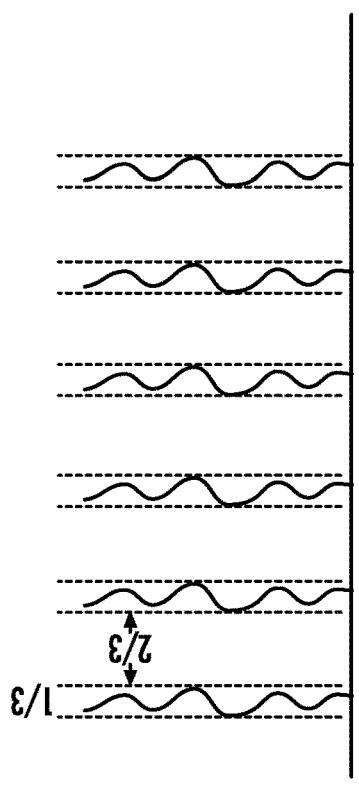
FIG. 3B is a schematic showing hypothetical cases of grafted polymers on a flat substrate in a mushroom configuration according to an embodiment.
Figure 3C:
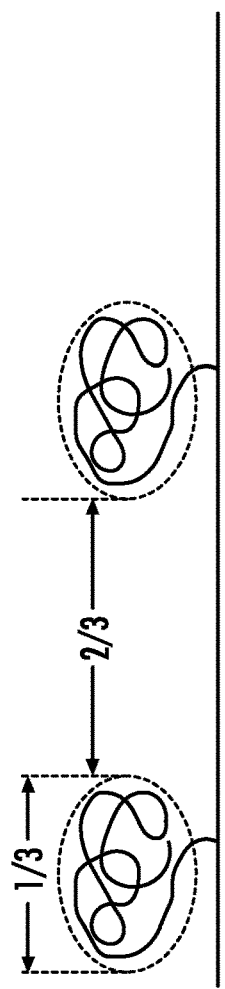
FIG. 3C is a schematic showing hypothetical cases of grafted polymers on a flat substrate in a mushroom configuration according to an embodiment.

Example geometries of grafted polymers on a flat substrate surface are shown in FIGS. 3A-3C, where the space between molecules is 2/3 of s, where s is the mean distance between molecules. The other 1/3 of the referenced length is occupied by the polymer itself. FIG. 3A shows the molecules in a brush configuration, while FIGS. 3B and 3C show the molecules in a mushroom configuration. The graft density of the polymer(s) adsorbed onto the substrate may be 1/3, as illustrated, or greater depending on the application. The graft density may range from 33% to 100%, e.g., 33, 35, 40, 50, 60, 70, 80, 90 or 100%, including ranges between any of the foregoing. A thickness of the grafted polymer coating may range from 10 nm to 10,000 nm, e.g., 10, 20, 50, 100, 200, 500, 1000, 2000, 5000 or 10,000 nm, including ranges between any of the foregoing. A grafted polymer coating may be un-cross-linked, partially cross-linked or fully cross-linked. The polymer coating may be formed by grafting PGA or alginate polymer, for example, to the substrate surface through charge interaction or covalent bonding.

In the absence of (or prior to) cross-linking, the grafted polymer forms a highly hydrated, non-fouling surface. A partially cross-linked or fully cross-linked grafted polymer will exhibit reduced mobility, which will enhance its accessibility to proteins and cells. In embodiments, a grafted polymer coating is at least partially cross-linked prior to cull culture. The degree of cross-linking may range from 1 to 100 mol %, e.g., 1, 2, 5, 10, 20, 50, 60, 70, 80, 90 or 100 mol %, including ranges between any of the foregoing. Prior to cell exposure, a cell adhesion layer is optionally formed over the polymer coating. Cells attach to and grow on the polymer coating via the cell adhesion layer. The thickness of a cell adhesion layer 400, when used, may range from 10 nm to 1 micron, e.g., 10, 20, 50, 100, 200, 500 or 1000 nm, including ranges between any of the foregoing. The cell adhesion layer may completely or partially cover the polymer coating.

Figure 1B:
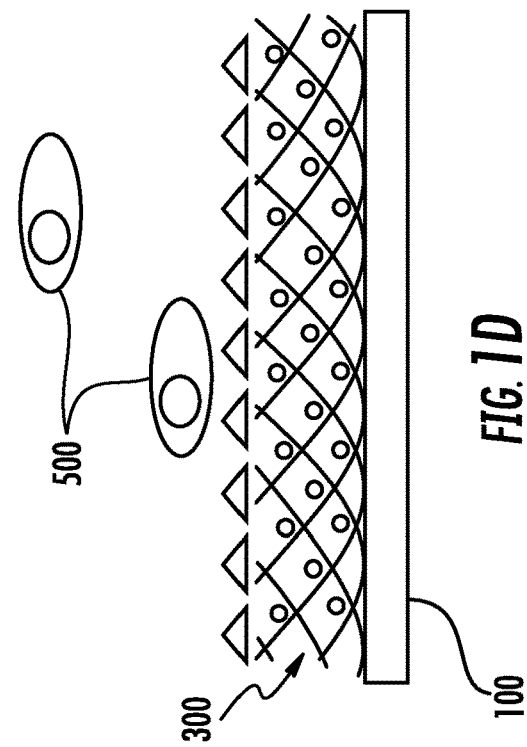
FIG. 1B is a schematic diagram of a substrate in which a grafted polymer coating is cross-linked using a divalent ion according to one embodiment.

With reference to FIG. 1A, illustrated is a substrate 100 having a grafted polymer coating 200 formed on a major surface 101 thereof. The grafted polymer coating 200 (e.g., after forming the grafted polymer coating on the substrate) may be cross-linked using a divalent ion such as calcium, for example, as shown in FIG. 1B. Calcium ions 600 are able to cross-link polymers such as PGA and alginate moieties because they can form two bonds (as opposed to monovalent ions such as sodium, which can form only a single bond). Suitable sources of calcium ions include calcium chloride and/or calcium carbonate. Cross-linking of the polymer coatings can minimize their dissolution into the cell culture medium.

Because calcium is incorporated into the polymer coating after its formation, the degree of cross-linking of the coating 300 can be non-uniform, with a higher degree of cross-linking near the free surface of the polymer, and a lesser degree of cross-linking through the coating thickness approaching the substrate.

Cross-linking is often measured by swelling experiments. A cross-linked sample is placed into a solvent at a specified temperature, and either the change in mass or the change in volume is measured. The extent of cross-linking is inversely proportional to the extent of swelling. Based on the degree of swelling, the Flory Interaction Parameter (which relates the solvent interaction with the sample), and the density of the solvent, a theoretical degree of crosslinking can be calculated according to Flory's Network Theory. ASTM Standard D2765 can be used to calculate the degree of cross-linking.

Figure 1C:
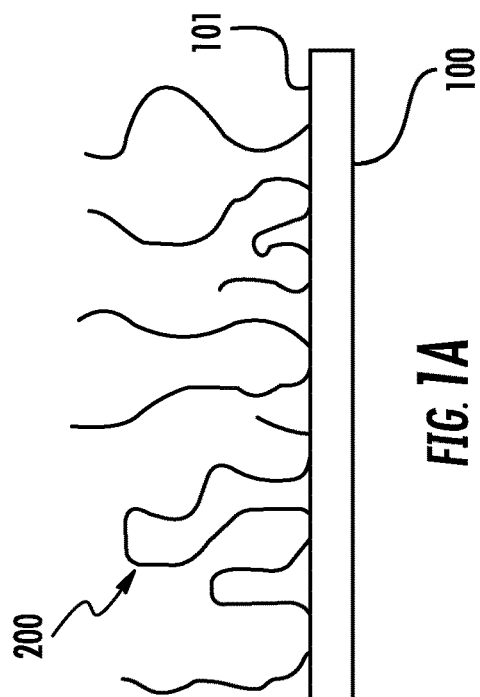
FIG. 1C is a schematic diagram of the polymer-coated substrate of FIG. 1B with a cell adhesion layer according to one embodiment.
Figure 1D:
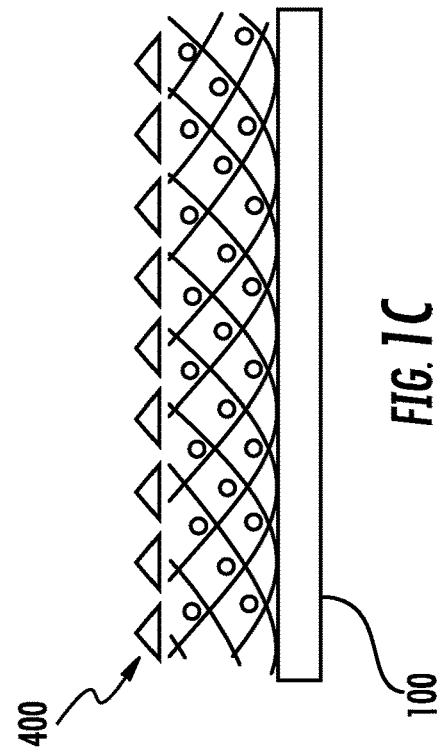
FIG. 1D is a schematic diagram of the polymer-coated substrate of FIG. 1C with cells being adhered to the cell adhesion layer according to one embodiment.
Figure 1F:
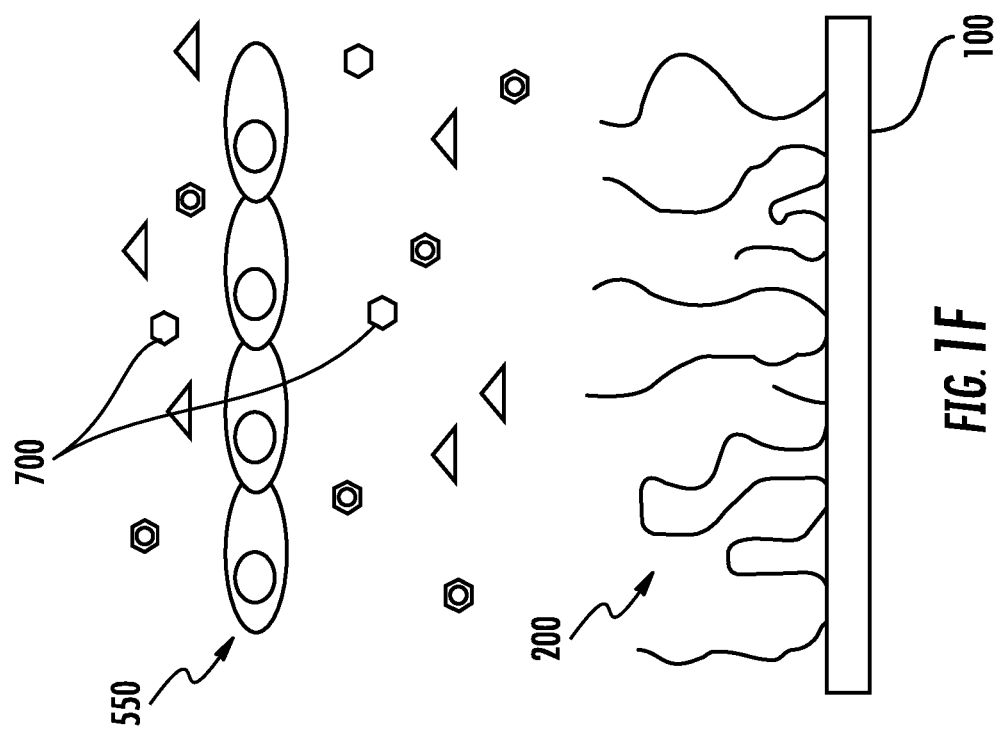
FIG. 1F is a schematic diagram of the polymer-coated substrate in a step of harvesting cells from the substrate according to one embodiment.
Figure 1E:
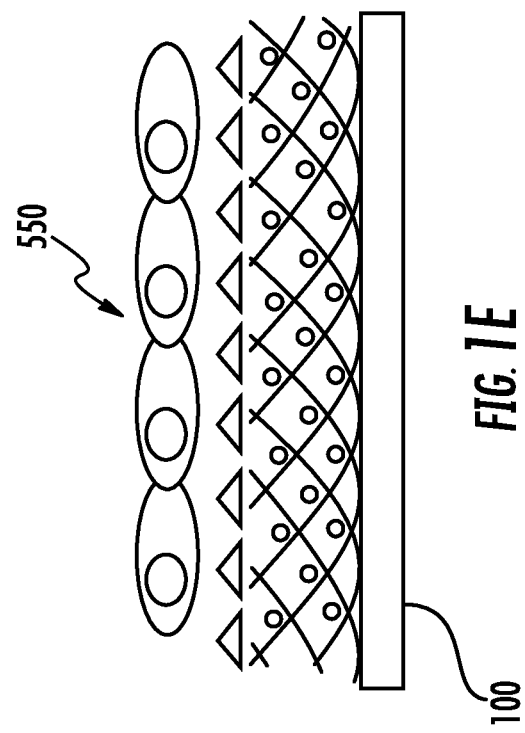
FIG. 1E is a schematic diagram of the polymer-coated substrate of FIG. 1C with cells adhered to the cell adhesion layer according to one embodiment.

As illustrated in FIG. 1C, a cell adhesion layer 400 may be formed over the grafted polymer that has been cross-linked 300. Cultured cells 500 bound to the cell adhesion layer 400 are shown schematically in FIGS. 1D and 1E. With particular reference to FIG. 1E, cells 500 form a cluster or colony 550 on the surface of the cell adhesion layer.

To harvest the cells, EDTA is added to the media. With reference to FIG. 1F, EDTA molecules 700 scavenge calcium ions 600 and return the polymer coating to a highly hydrophobic, non-fouling state. The cultured cells will be released into the media as colonies or cell sheets 550. Release and harvesting of the cultured cells is performed in the absence of proteinase.

The grafted polymer coating 200 in FIG. 1F can be recycled (i.e., re-introduced to the protocol at FIG. 1A). The grafted polymer coating can be re-cross-linked and a new cell adhesion layer can be formed over the grafted polymer coating in advance of a further cycle of cell attachment, cell growth and cell harvesting.

In a further embodiment, a 0.5 micron to 1000 micron thick polymer coating is uniformly cross-linked on a substrate. The thickness of the polymer coating may be 0.5, 1, 20, 5, 10, 20, 50, 100, 200, 500 or 1000 microns, including ranges between any of the foregoing. The degree of cross-linking may range from 1 to 100 mol %, e.g., 1, 2, 5, 10, 20, 50, 60, 70, 80, 90 or 100 mol %, including ranges between any of the foregoing.

The polymer coating may be formed by mixing a water solution of PGA or alginate with $CaCO_3$ powder to form a suspension that is applied to a surface of the substrate. The suspension may optionally include a surfactant or solvent (in addition to water) to promote the formation of a thin coating. The coating is exposed to acetic acid vapor, which reacts with the $CaCO_3$ to release $Ca^{2+}$ ions that, in turn, bind to the PGA or alginate polymer and cross-link the polymer. Evaporation of the water, surfactant and/or solvent may occur before, during or after gelation (cross-linking).

Prior to introducing the cells and growth media, a cell adhesion layer is optionally formed over the cross-linked polymer coating. Cells attach to and grow on the polymer coating via the cell adhesion layer. In embodiments, cells are cultured in direct physical contact with the cell adhesion layer.

To harvest the cells, EDTA is added to the growth media. The EDTA scavenges the calcium and compromises the cross-linking of the polymer. Optionally, pectinase or alginate lysase may be introduced to the media to proactively cleave the polymer bonds and expedite dissolution or digestion of the polymer coating. The combination of cross-linking annihilation by EDTA and cleavage by enzyme make the process very fast, which minimizes the negative impact to the cell product. As a result, cells will be released into the media as colonies or cell sheets. In the absence of proteinase, the integrity of cell-to-cell interactions in the released cells is preserved.

Figure 2A:
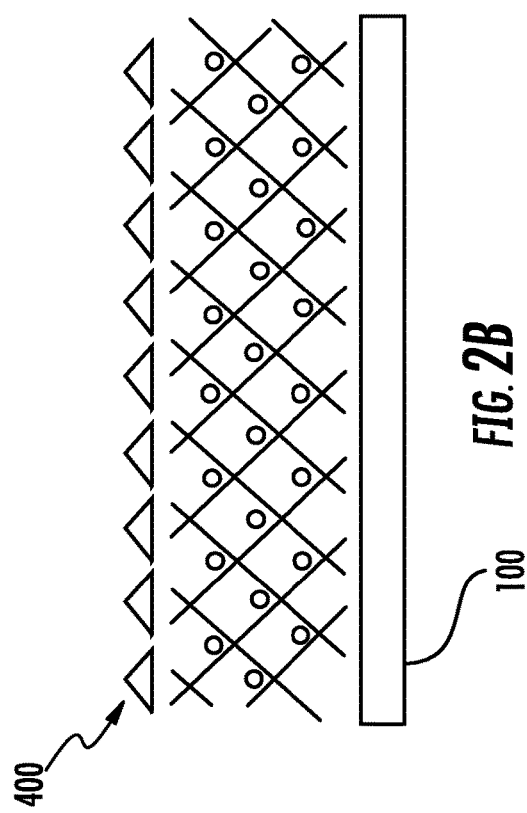
FIG. 2A is a schematic diagram of a polymer-coated substrate and its method of use according to a further embodiment.
Figure 2B:
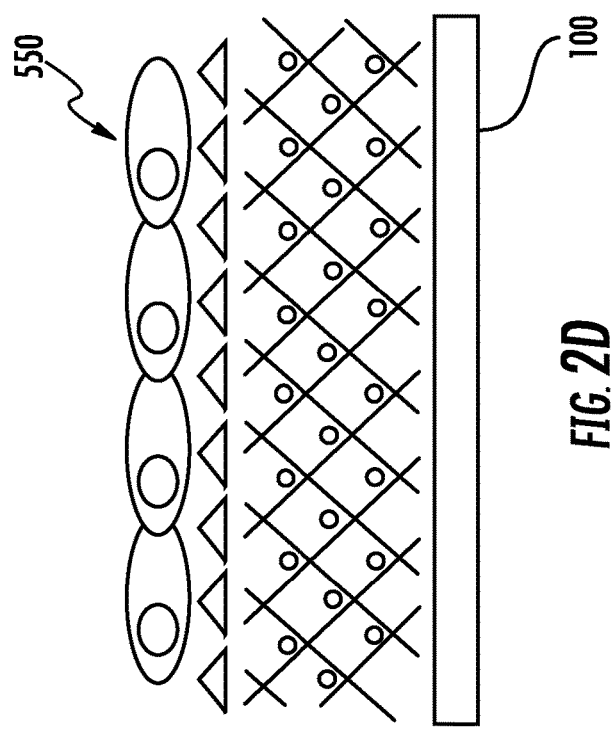
FIG. 2B is a schematic diagram of a polymer-coated substrate having a cell adhesion layer according to an embodiment.
Figure 2C:
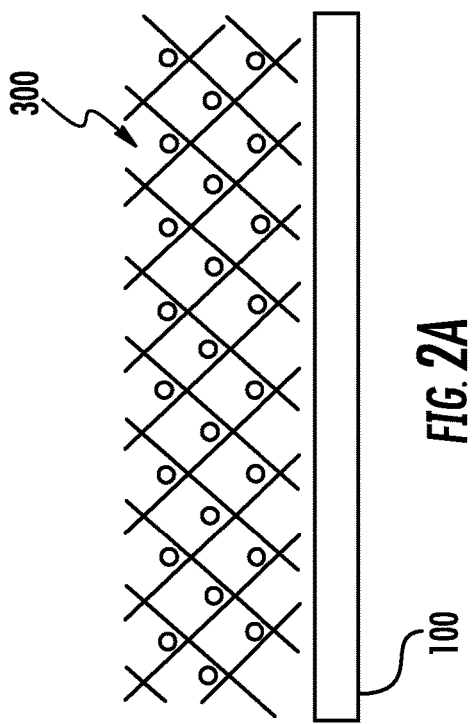
FIG. 2C is a schematic diagram of a polymer-coated substrate with cells being adhered to a cell adhesion layer according to an embodiment.
Figure 2D:
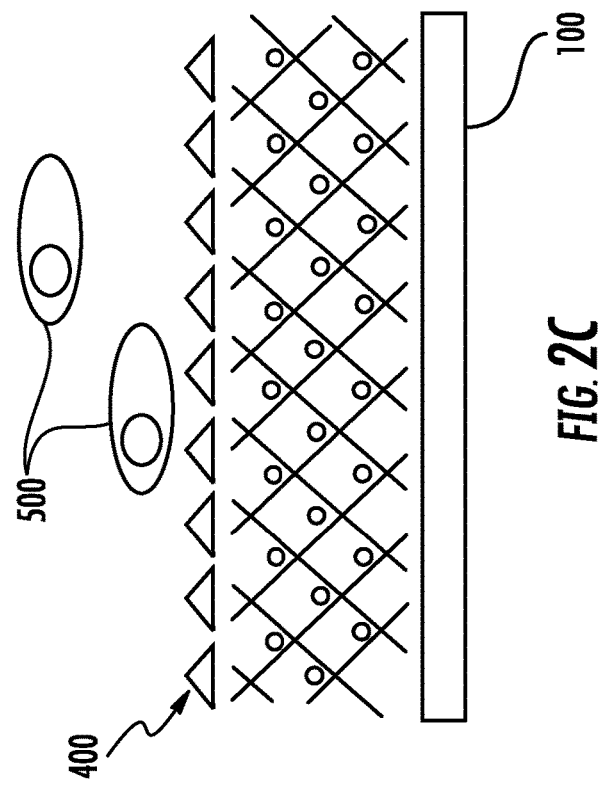
FIG. 2D is a schematic diagram of a polymer-coated substrate with cells adhered to a cell adhesion layer according to an embodiment.

In FIG. 2A is illustrated a substrate 100 having a cross-linked polymer coating 300 formed on a major surface thereof. Because calcium is incorporated in situ into the polymer coating, the degree of cross-linking of the coating 300 can be uniform throughout the coating thickness. As illustrated in FIG. 2B, a cell adhesion layer 400 may be formed over cross-linked polymer coating 300. Cultured cells 500 bound to the cell adhesion layer 400 are shown in FIGS. 2C and 2D. Individual cells 500 form a cluster or colony 550, as depicted in FIG. 2D.

With reference to FIG. 2E, pectinase or alginate lysase 800 in conjunction with EDTA 700 may at least partially digest the polymer coating to release the cell cluster 550 in tact from the substrate 100. The cell adhesion layer 400 may disassociate in conjunction with digestion of the polymer layer.

The polymer-coated substrates disclosed herein enable cell expansion in any suitable growth medium. Example media include chemically-defined media, serum-containing media, and serum-free media. The polymer-coated substrates can be used to culture cells as cell sheets, for example, for tissue engineering or organ reconstruction. Once cell growth is complete, EDTA or another chelating agent optionally in combination with an enzyme such as pectinase or alginate lysase, is used to un-cross-link or at least partially digest the polymer coating such that the cultured cells are separated from the underlying substrate. Cell-to-cell interactions are sustained such that the cluster or colony is maintained.

Figure 4:
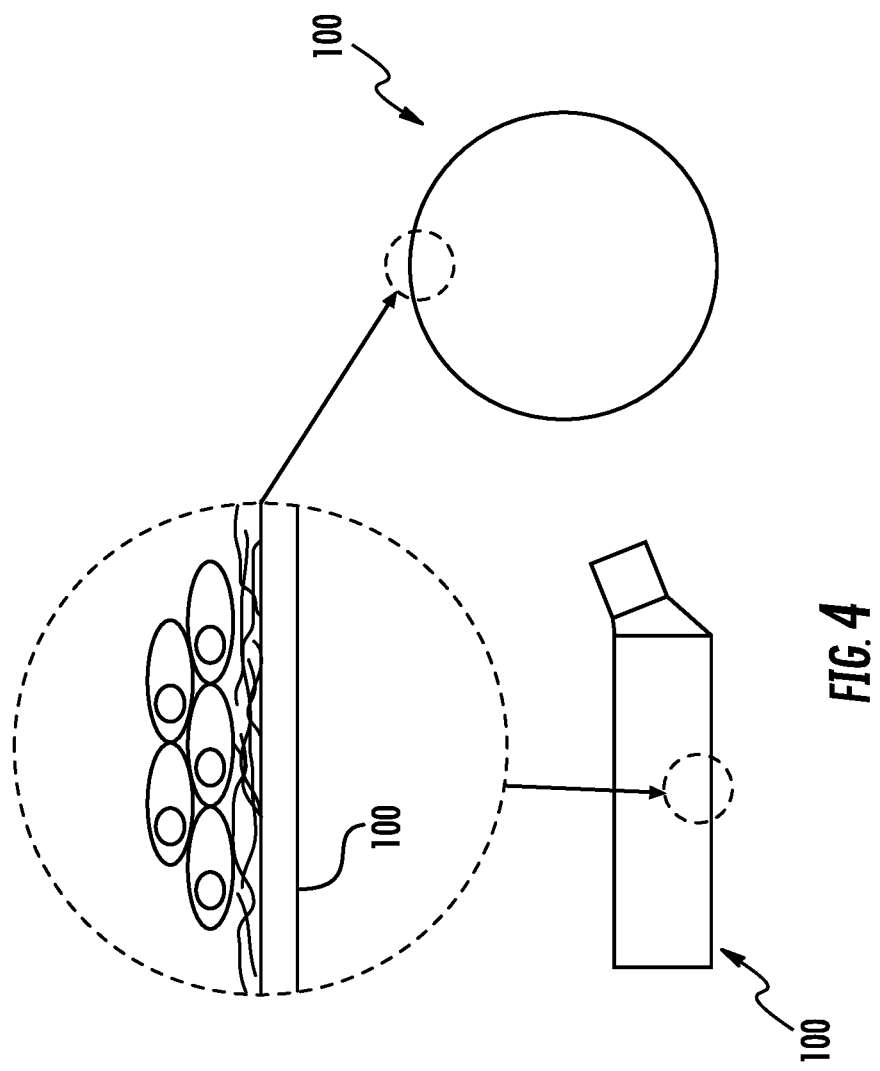
FIG. 4 shows example polymer-coated substrate assemblies.

As illustrated in FIG. 4, the herein-disclosed cell harvesting protocol may be carried out by forming the polymer coating on the surface of a flask or a microcarrier bead.

EXAMPLES

A. Grafting PGA-VN

As one approach to obtain a PGA polymer functionalized with peptide, we investigated the possibility of coating poly lysine plates (PLL) with PGA. The PGA is then cross-linked by the action of $CaCl_2$ and VN peptide is grafted using EDC/NHS.

Data obtained on the peptide surface shows a correlation between peptide density and the quality of cell adhesion. Chemical characterizations were performed to define the grafting conditions that allow the highest peptide density on the PGA surface. The impact of EDC/NHS ratio and peptide concentration were evaluated.

Figure 5A:
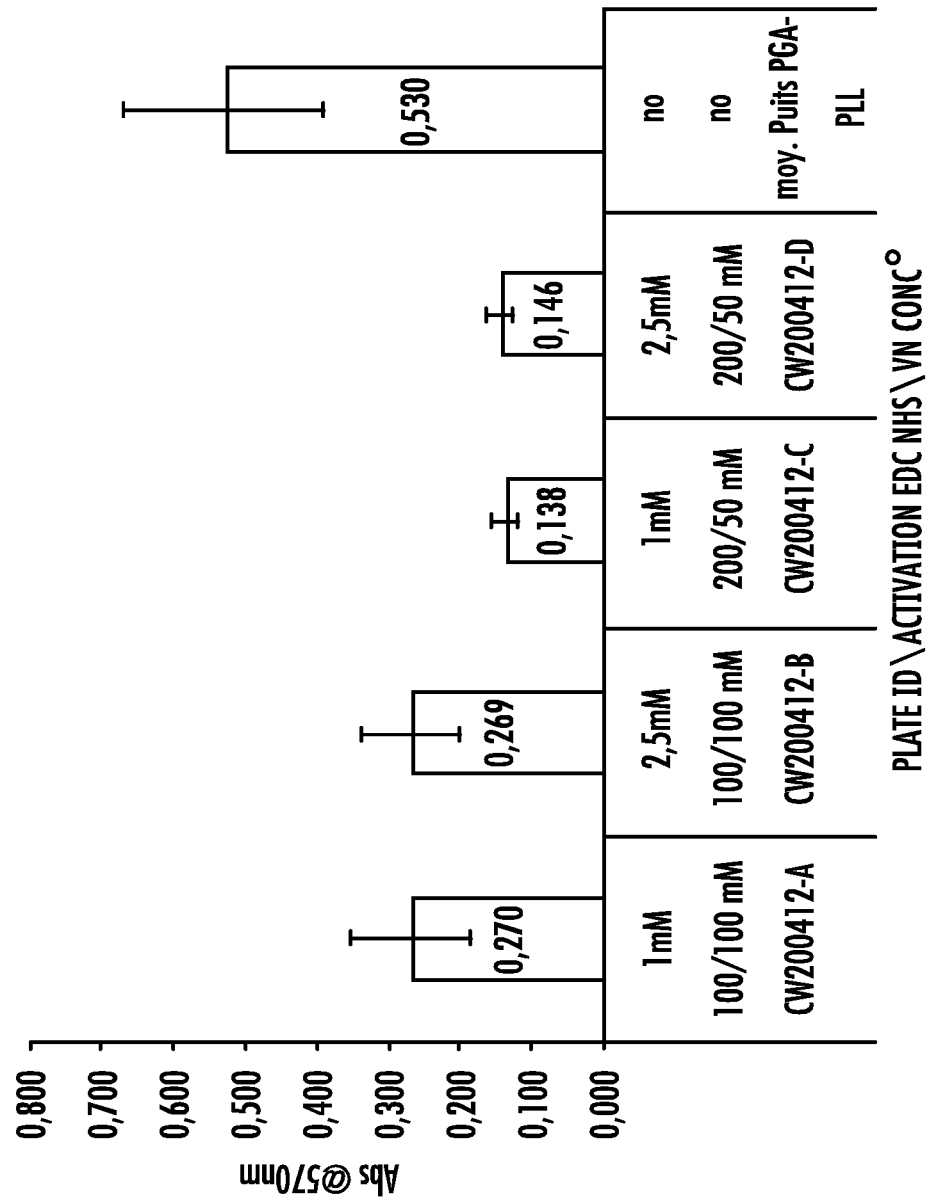
FIG. 5A shows absorbance results of gold staining for VN grafted onto PGA.
Figure 5B:
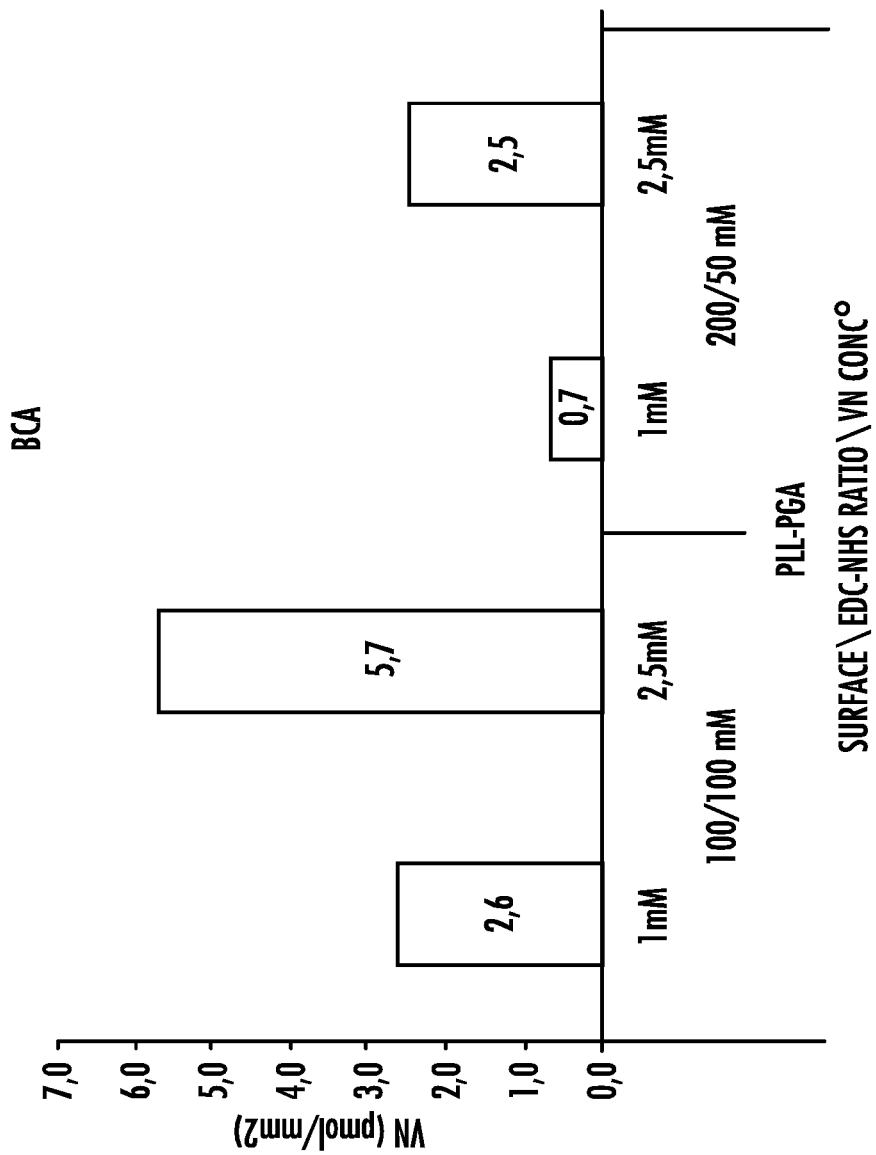
FIG. 5B shows BCA results for VN grafted onto PGA.

FIGS. 5A and 5B show gold staining and BCA quantification of VN peptide grafted on PLL-PGA as a function of EDC/NHS ratio and VN peptide concentration.

From the FIG. 5 data, we can conclude that the surface with the highest peptide density is obtained with a VN concentration of 2.5 mM using EDC:NHS of 100 mM:100 mM.

The surfaces were tested with ES-D3 cells in a xeno-free medium. The quality of adhesion of this cell line is generally correlated to peptide concentration and facilitates evaluation of peptide availability.

Figure 6:
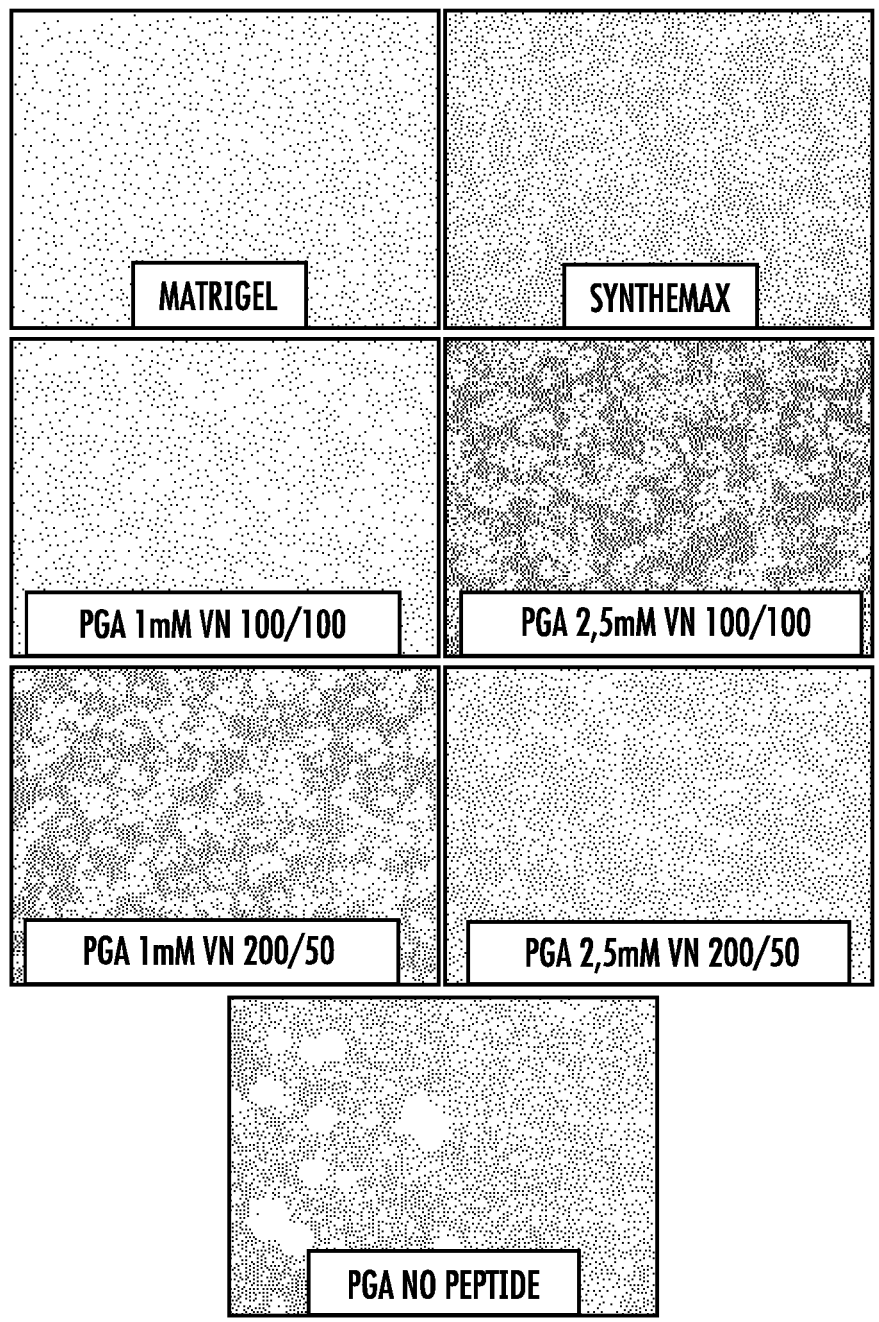
FIG. 6 are phase contract micrographs illustrating ES-D3 cell adhesion on various surfaces according to embodiments.

Phase contrast microscopy images illustrating ES-D3 cell adhesion after 18 hours on control and VN-grafted PGA surfaces as a function of peptide concentration and EDC/NHS ratio are shown in FIG. 6.

PGA plates prepared with different peptide concentrations (1 mM and 2.5 mM) grafted using different ratios of EDC/NHS (100:100 and 200:50) were tested and cell adhesion was compared to Matrigel™ matrix coated plates or Synthemax® surfaces. Cell morphology on PLL-PGA plates grafted with 2.5 mM of VN peptide using EDC/NHS 100:100 is comparable with the morphology on the Synthemax® surface. Cell adhesion is observed for other conditions, but was inferior to the Synthemax® surface. No adhesion is observed in the absence of the peptide.

The foregoing plates were tested with hMSC in a xeno-free medium (XF medium). Good cell adhesion and cell growth were observed on all the surfaces grafted with peptide.

Figure 7:
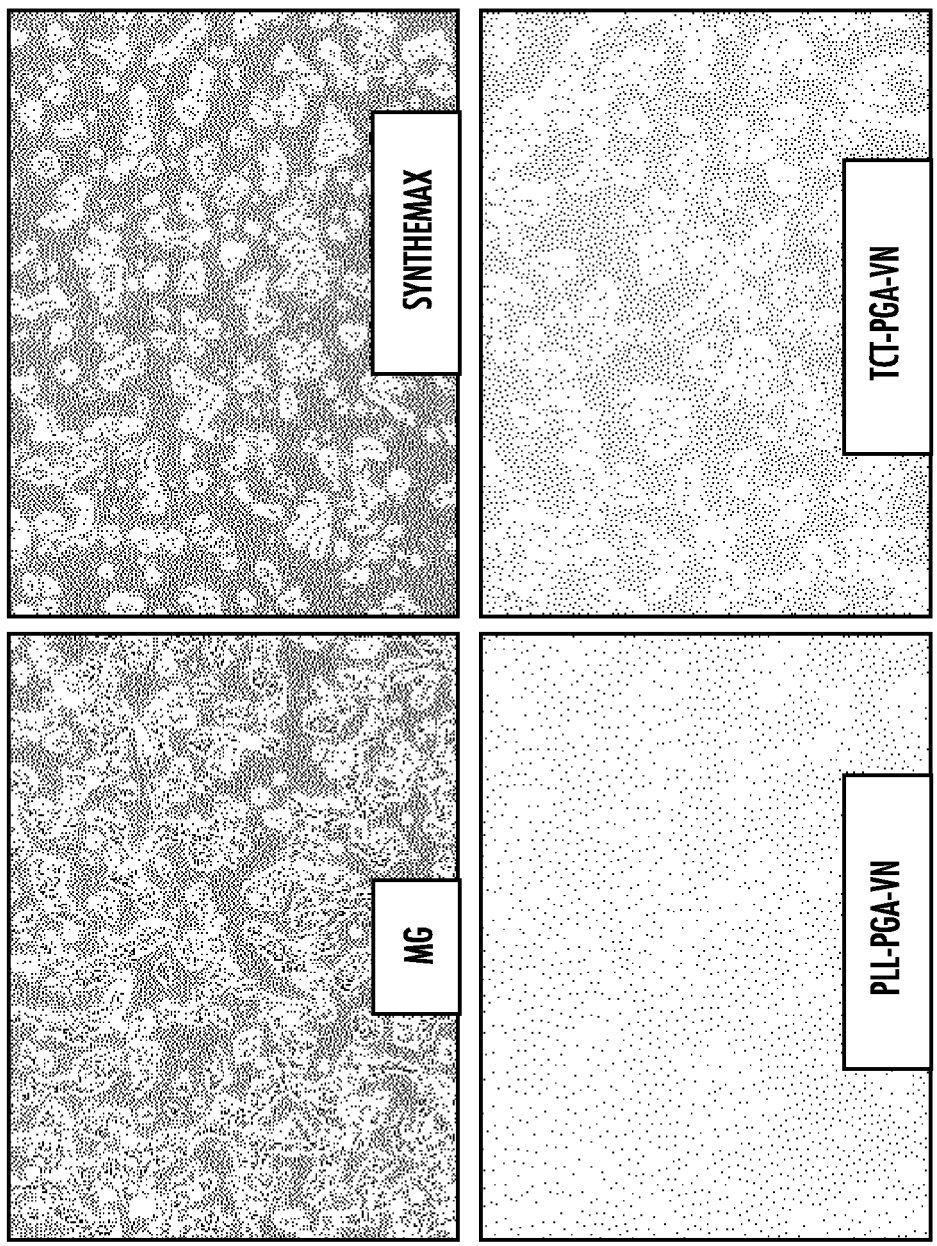
FIG. 7 are phase contrast micrographs illustrating ES-D3 cell adhesion on various substrates according to embodiments.

A further test was conducted with ES-D3 cells to evaluate the impact of the PLL substrate and to compare PLL-PGA-VN (1 mM VN, EDC/NHS 100:100) plates with PGA-VN (1 mM VN, EDC/NHS 100:100). The results presented in FIG. 7, which shows phase contrast micrographs illustrating ES-D3 cell adhesion at 18 hours on control and VN grafted PGA surfaces coated on PLL or TCT, indicate that the removal of PLL has no negative impact on ES-D3 cell adhesion and improves slightly the spreading of the cells.

Figure 8:
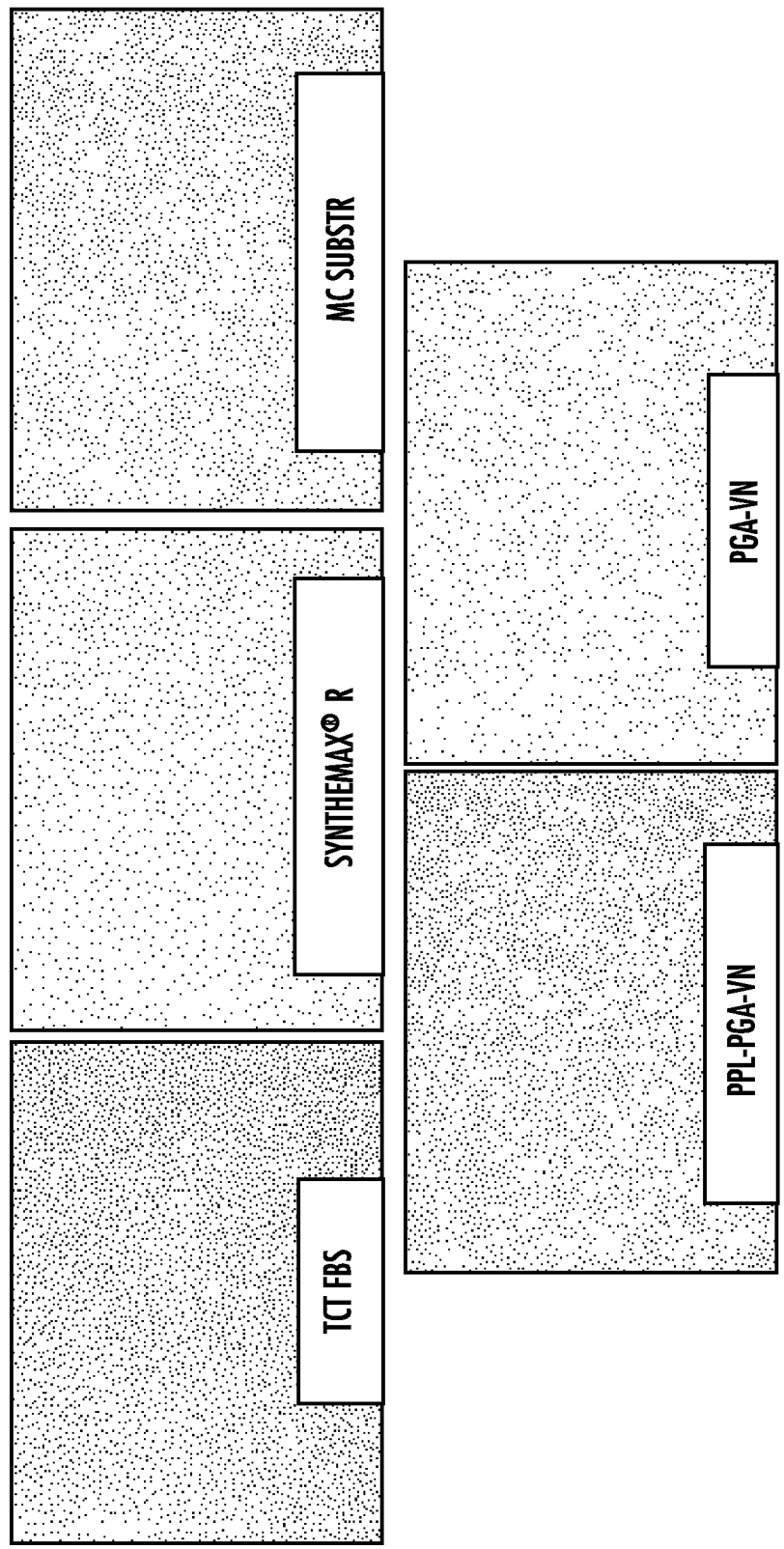
FIG. 8 are phase contrast micrographs illustrating hMSC adhesion on various substrates according to embodiments.
Figure 9A:
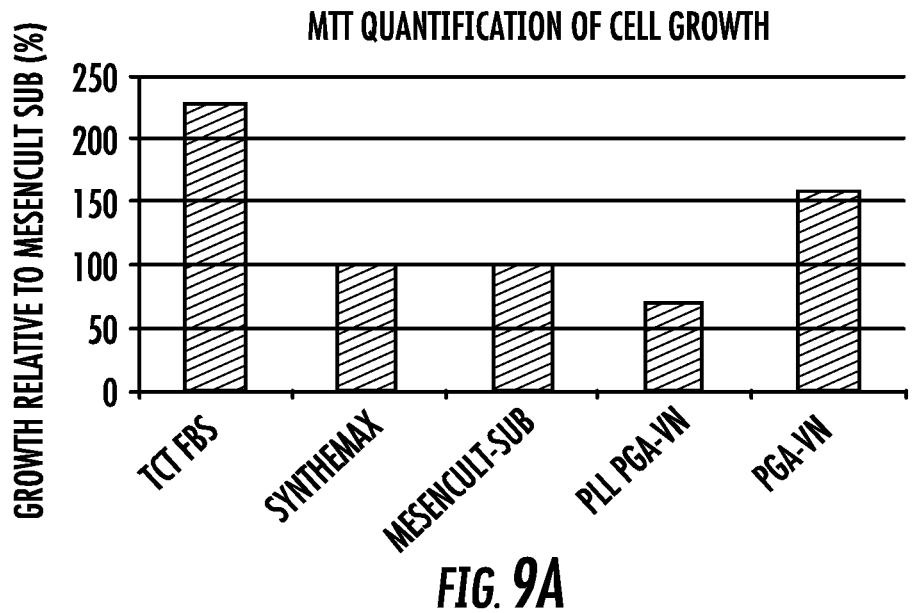
FIG. 9A shows MTT quantification of cell number relative to the reference mesencult substrate plate.
Figure 9B:
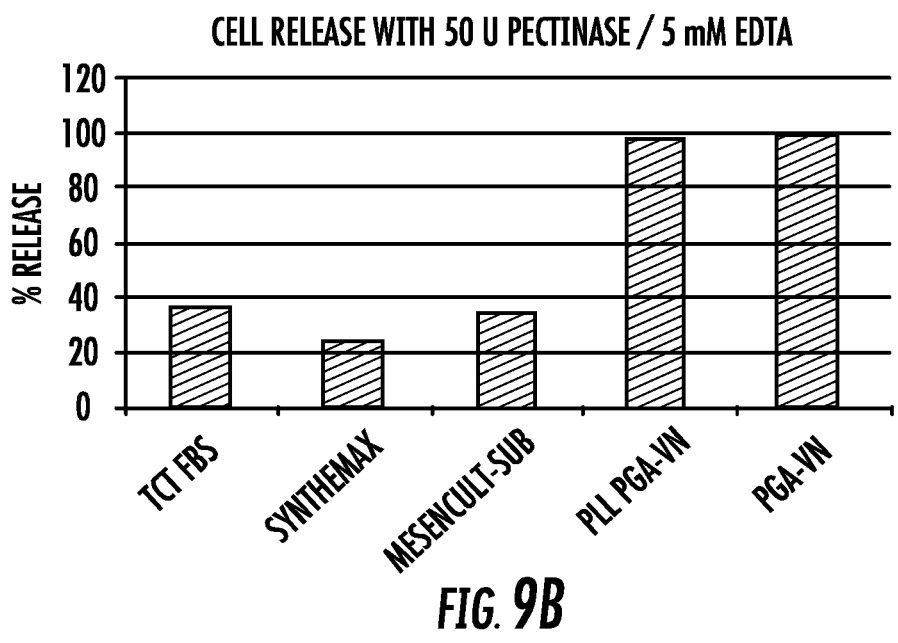
FIG. 9B shows the efficiency of cell release using pectinase/EDTA treatment.

The foregoing plates were then evaluated with hMSC. The phase contrast microscopy data in FIG. 8, which illustrates hMSC adhesion and growth after 5 days on control and VN grafted PGA surfaces, show that the growth obtained after 5 days on PGA-VN plates is slightly better than what is observed on Synthemax® surfaces or Mesencult (MC) substrate coated plates. On PLL-PGA-VN plates, the cell growth observed is below the references. With reference to FIG. 9A, cell growth was quantified using MTT assay. The data confirm the results of observations with cell growth on PGA-VN exceeding what is obtained on reference plates (Synthemax and Mesencult substrate). Cell release was attempted with a pectinase/EDTA mix on all surfaces, and the efficiency of the cell release is summarized in FIG. 9B. The release is complete for the PGA based surfaces, but does not reach more than 40% on the other surface types.

PGA-based surfaces, in embodiments are designed to allow protease-free cell release with a pectinase/EDTA solution. The action of EDTA induces a disruption of PGA cross-linking by chelation of calcium ions, and a perturbation of cell-cell and cell-ECM interactions, while pectinase digests the PGA chains. The action of both compounds is associative; it degrades the PGA-VN polymer and induces cell release.

Figure 10:
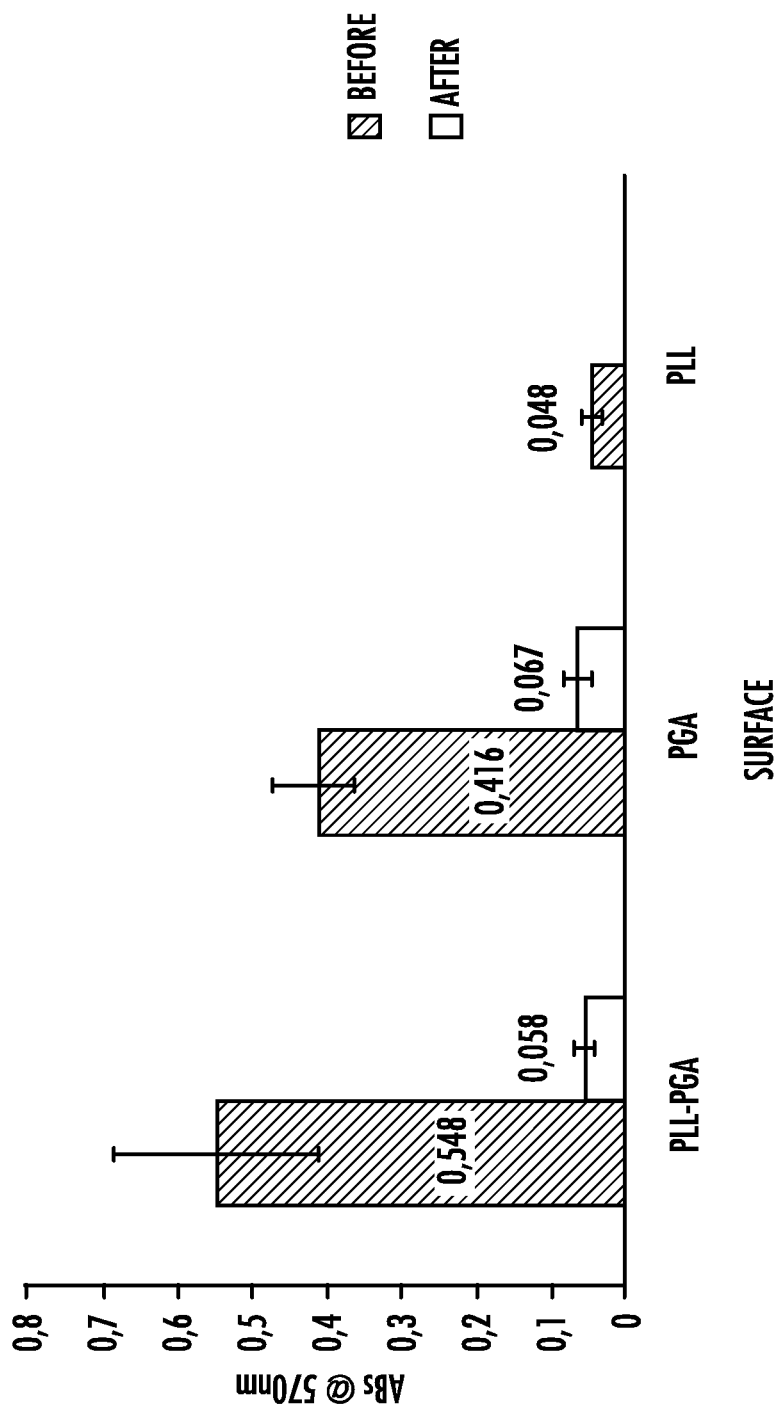
FIG. 10 are absorbance results of crystal violet staining on PGA-based surfaces before and after pectinase/EDTA treatment.

The results presented in FIG. 10 demonstrate, using CV staining, that the PGA surface is degraded after pectinase/EDTA treatment.

Figure 11:
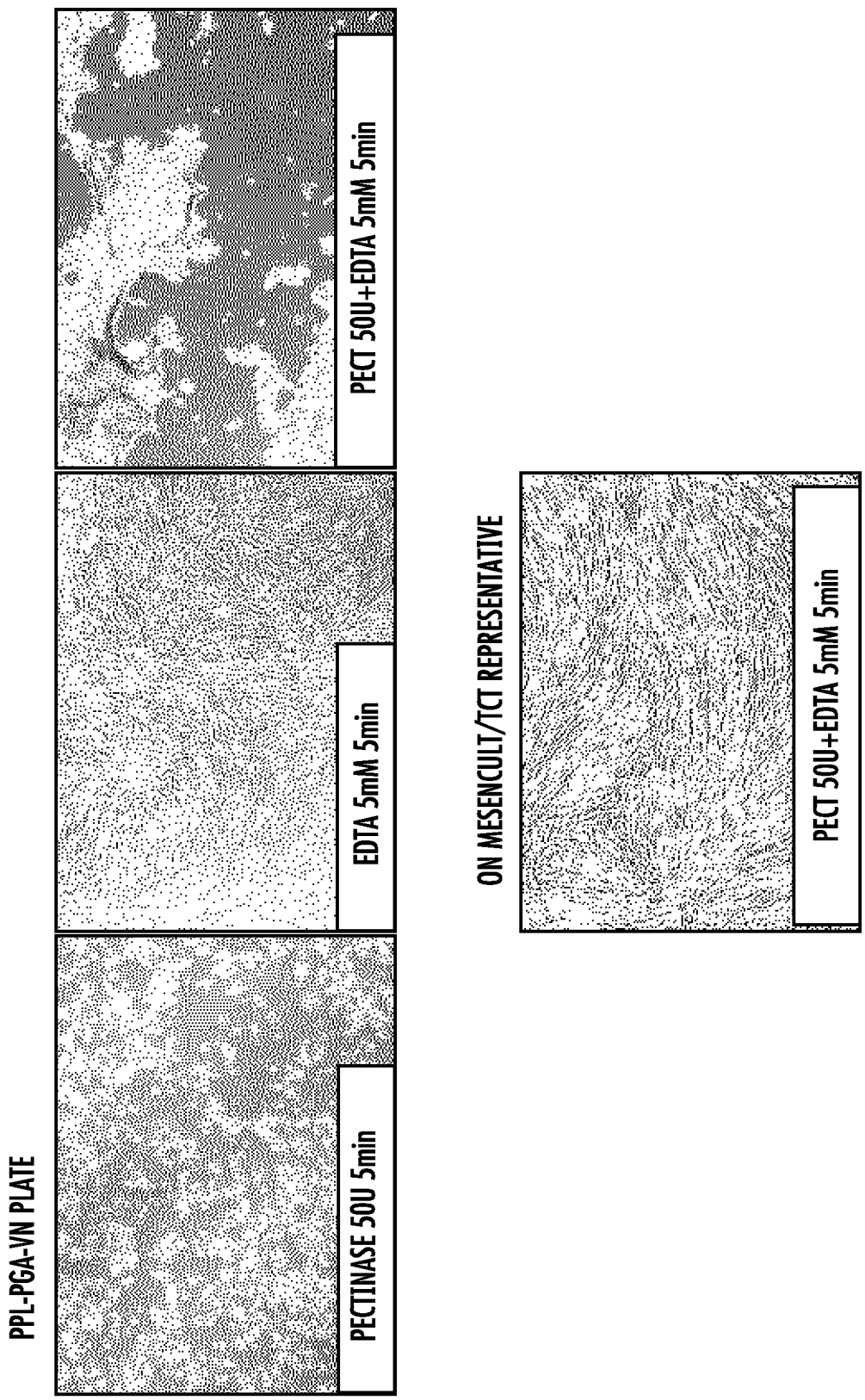
FIG. 11 shows phase contrast micrographs illustrating the effect of treatment with pectinase, EDTA, or the combination of pectinase and EDTA.

FIG. 11 is phase contrast microscopy images illustrating the effect of a 5 minute treatment with pectinase, EDTA, or pectinase EDTA mixtures on VN grafted PGA or on Mesencult™ substrate coated plates. A 5 minute treatment with pectinase alone alters cell adhesion but is not sufficient to completely release the cells. EDTA treatment alone has a minor effect on cell adhesion. However, a 5 minute treatment with a pectinase/EDTA mixture induces a complete release of the cell from the PGA based polymer, while the same treatment has no effect on cells adhering to TCT on a Mesencult™ substrate.

Figure 12:
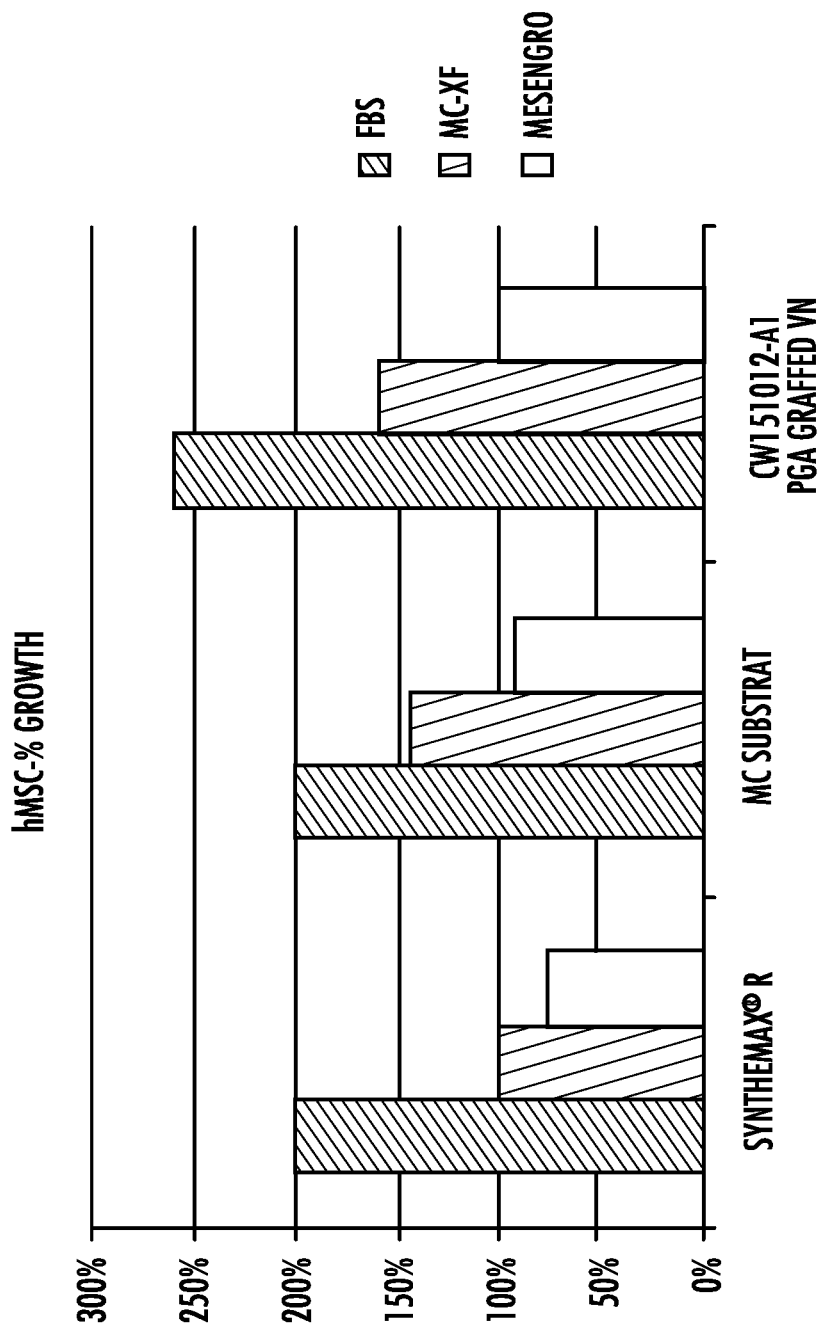
FIG. 12 is a chart quantifying hMSC growth according to various embodiments.

Using the grafting approach to attach the cell adhesion layer to the polymer coating, we developed a surface for which a PGA polymer is coated on TCT. After cross-linking with $CaCl_2$, VN peptide is grafted using EDC/NHS chemistry. As illustrated in FIG. 12, the performance of this surface for the growth of hMSC exceeds what is obtained with Synthemax® substrates or Mesencult™ substrates (a bio-coating) irrespective of the culture medium: FBS containing medium, Mesencult™ XF medium, or StemGro® (MesenGro®) medium.

In various embodiments, complete cell release is obtained in 5 minutes in the absence of proteases using a pectinase/EDTA solution.

B. Polymer Coatings and Adhesion-Promoting Layers

Figure 13A:
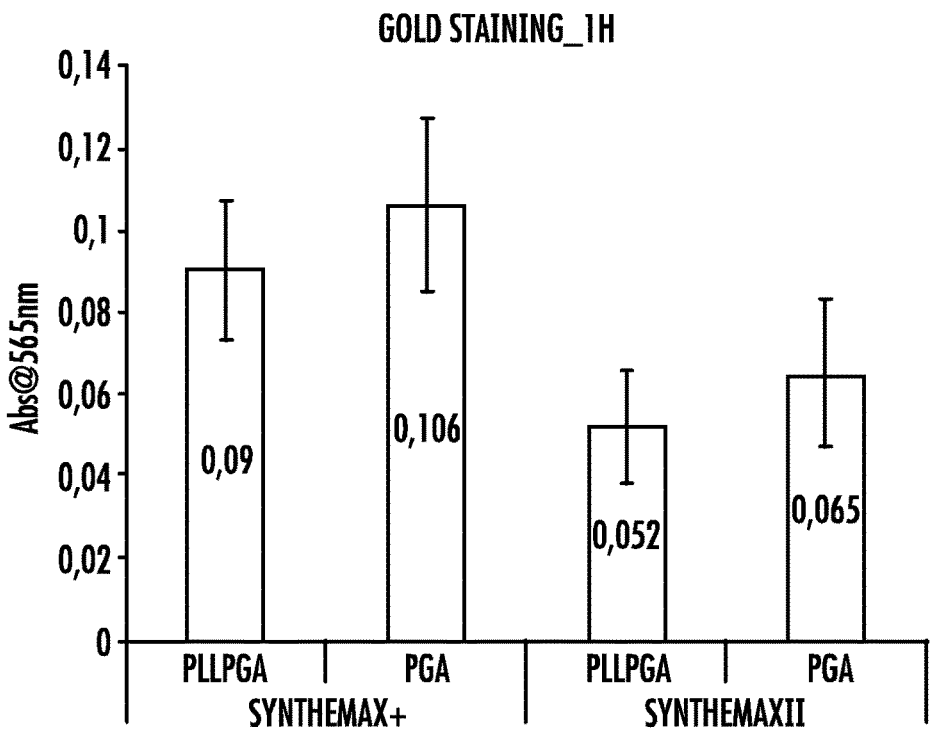
FIGS. 13A and 13B show absorbance data and BCA data for cross-linked PGA or cross-linked PGA-PLL coatings provided with layers of either Synthemax+ or Synthemax II.
Figure 13B:
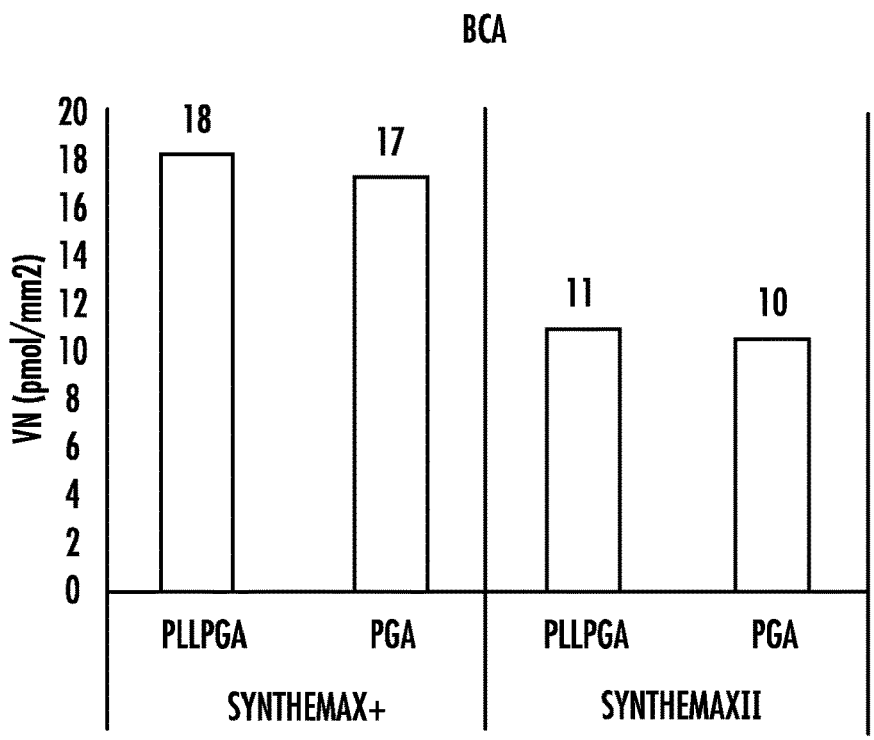

According to one embodiment, an adhesive layer comprising VNARGPEGMAAcoHEMA copolymer (Synthemax+, positively charged) was formed on a cross-linked PGA polymer coating on PLL or TCT substrates. Chemical characterization of the PGA surfaces coated with Synthemax+ was performed in comparison with Synthemax II (VNPEGMAAcoHEMA) coatings. Absorbance results of gold staining and BCA data are summarized in FIG. 13.

The highest peptide density is obtained with Synthemax II, though comparable cell growth is obtained for each of PGA and PLL-PGA.

Figure 14:
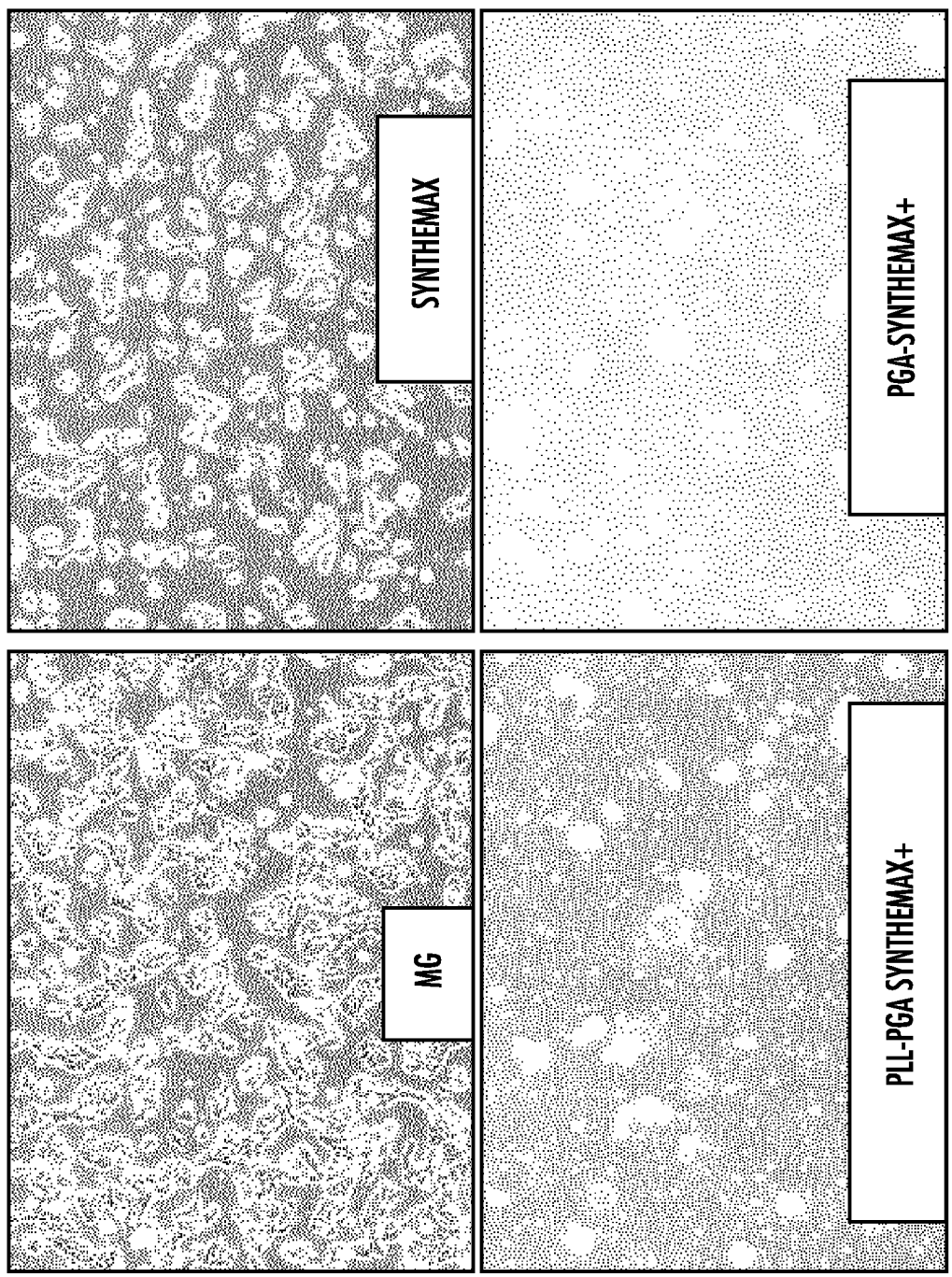
FIG. 14 shows phase contrast micrographs illustrating ES-D3 cell adhesion on control and Synthemax+ coated PGA substrates.

The plates prepared were tested with ES-D3 cells. The results obtained are presented in the phase contrast images of FIG. 14, which shows generally poor cell adhesion.

Figure 15:
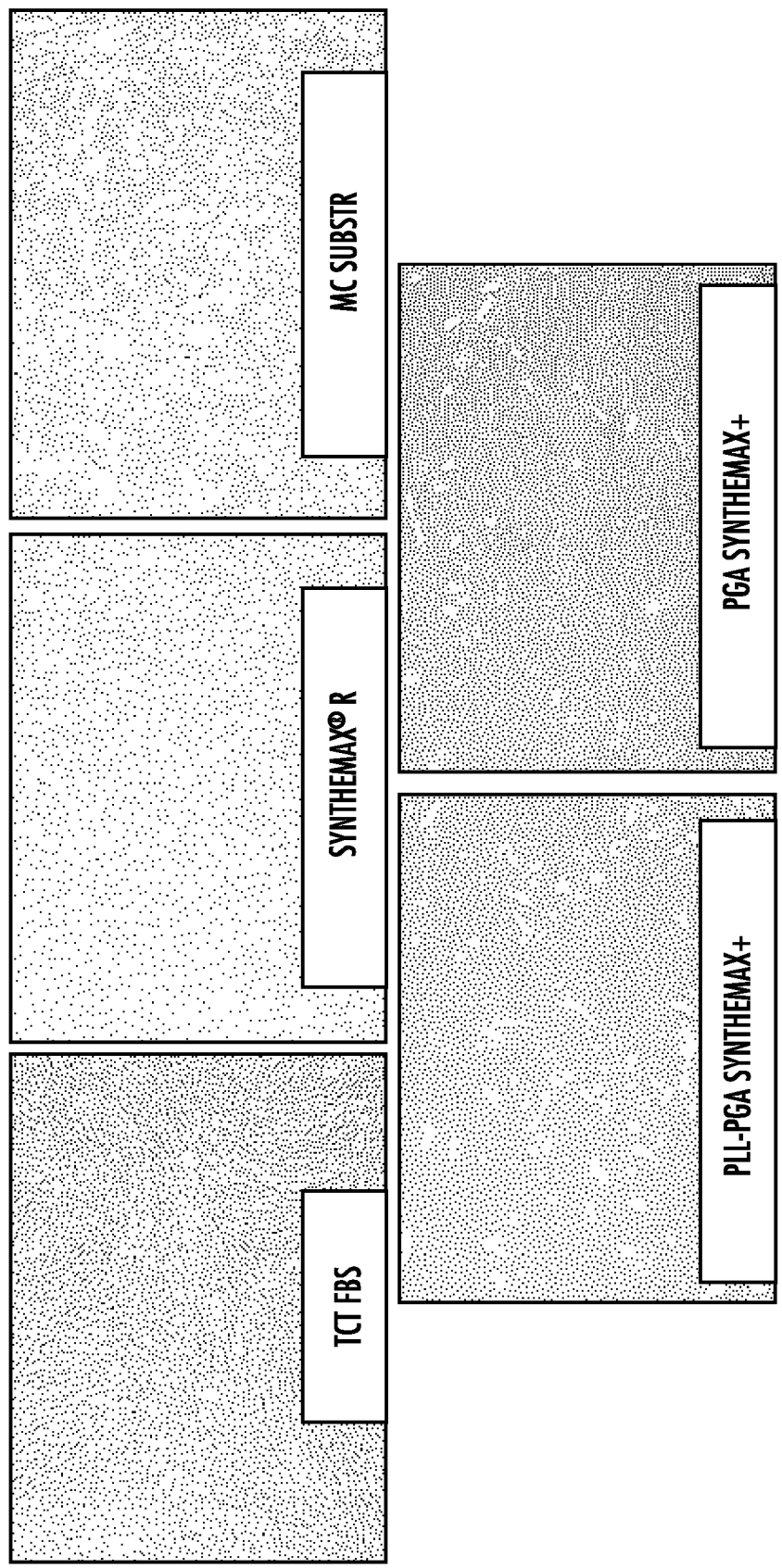
FIG. 15 shows phase contrast micrographs illustrating hMSC cell adhesion on control and Synthemax+ coated PGA substrates.

The same experiment was repeated with hMSC. As with the ES-D3 cells, poor cell adhesion was observed, as depicted in the phase contrast micrographs of FIG. 15, which show hMSC adhesion and growth at day 5 on control and Synthemax+ coated PGA surfaces formed on PLL or TCT substrates. Similar results were obtained when using Synthemax II in lieu of Synthemax+.

Synthemax layers on PGA polymer coatings provide surfaces with a high peptide density (more than 10 pmol/$mm^2$ versus 5 pmol/$mm^2$ for the reference, Synthemax® R) but do not facilitate good cell adhesion.

Experiments to improve cell adhesion focused on a PGA/SynthemaxII blend.

According to a further embodiment, a PGA/SynthemaxII blend is used to coat plates by adsorption (KB process or cast and cure), following which the polymer coating is cross-linked using $CaCl_2$.

For a cast and cure process, in order to see the impact of the $Ca^{2+}$ cross-linking a surface was prepared without a $CaCl_2$ incubation step.

Figure 16:
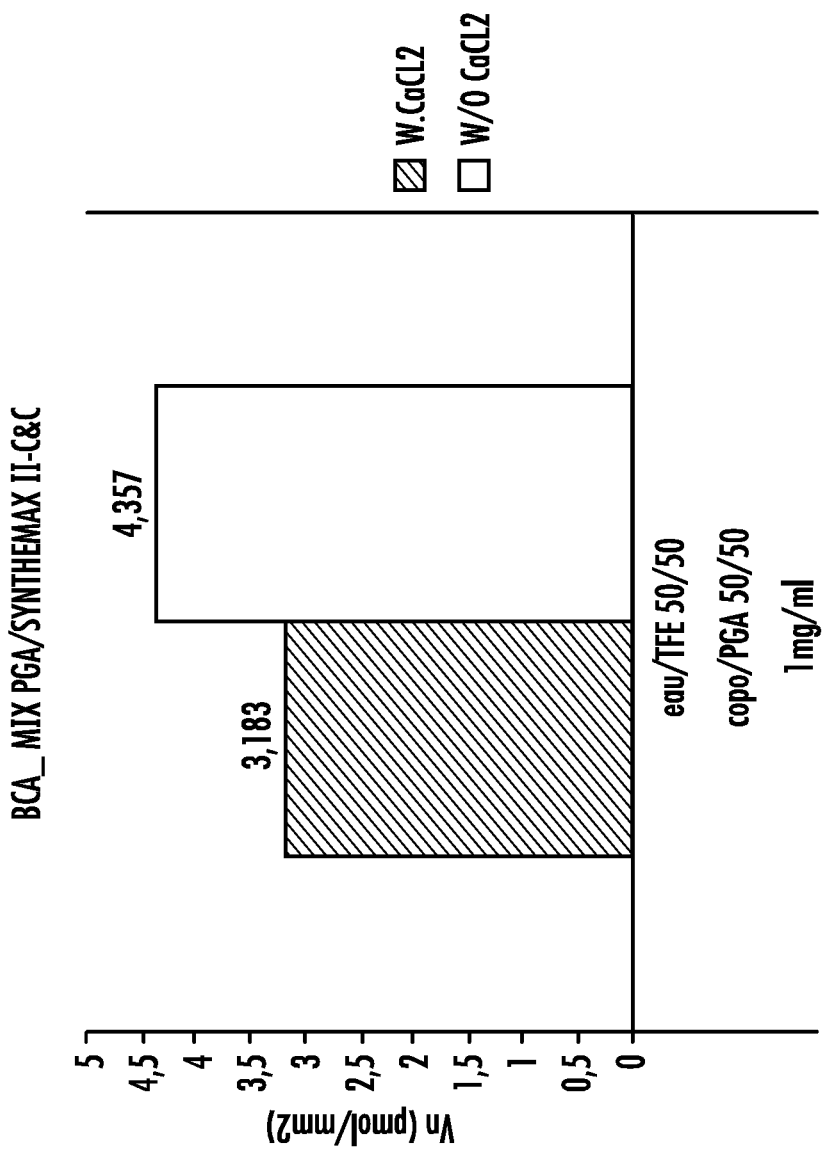
FIG. 16 shows BCA data for coatings prepared with and without cross-linking using a cast and cure process.

FIG. 16 shows BCA results for surfaces prepared with and without cross-linking using the cast and cure process. The data indicate that there is no significant impact on the peptide concentration adsorbed on surface.

Figure 17:
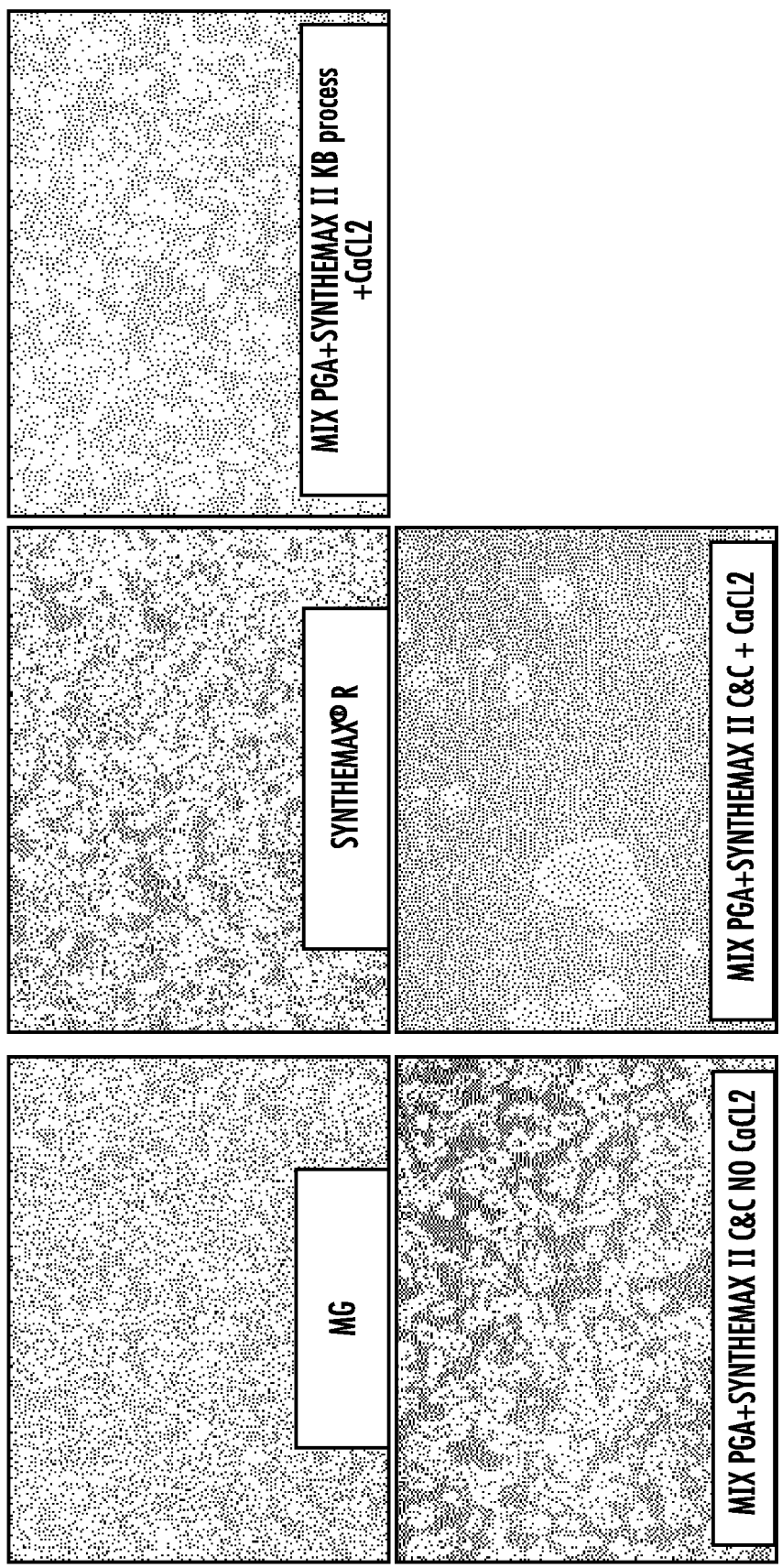
FIG. 17 shows phase contrast micrographs illustrating ES-D3 adhesion on control and mixed PGA/Synthemax coated substrates.

The results obtained with ES-D3 cells are presented in FIG. 17. When the surface is prepared with the KB process, cell adhesion is observed but is likely correlated to the adsorption of Synthemax polymer only. With the cast and cure process, however, good cell adhesion is observed when the polymer blend is not cross-linked with $CaCl_2$. Cell adhesion is lost after cross-linking the polymer blend.

Figure 18:
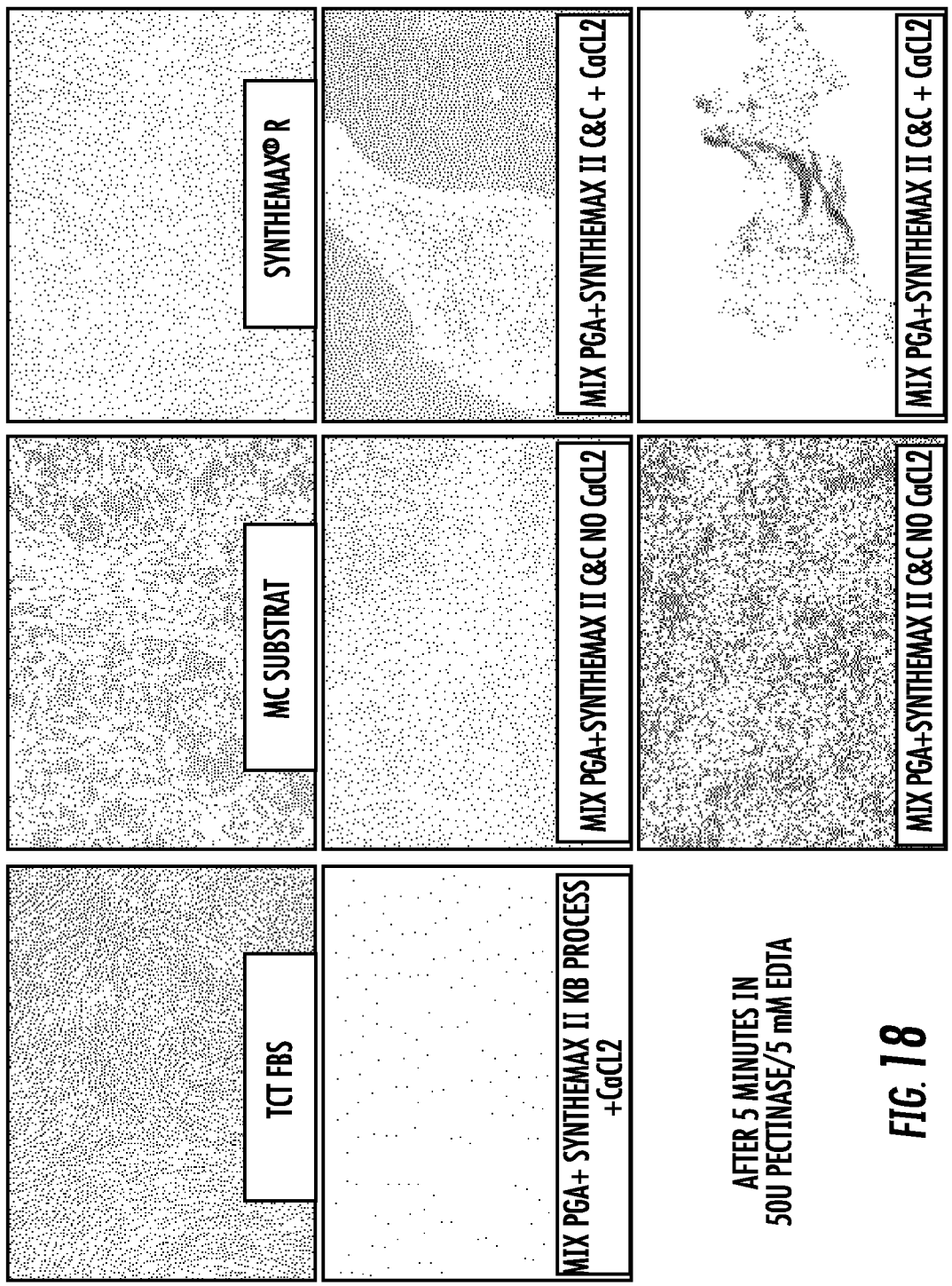
FIG. 18 shows phase contrast micrographs illustrating hMSC adhesion on control and mixed PGA/Synthemax coated substrates.

The foregoing surfaces were tested with hMSC, and the results of cell growth after 5 days are presented in FIG. 18. With the hMSC cells, as with the ES-D3 cells, some adhesion and growth are observed with the KB process, and adhesion and growth is observed with the cast and cure process in the absence of cross-linking, but adhesion is lost when the polymer blend is cross-linked.

Cell release was promoted with pectinase/EDTA. For the cast and cure plates, cells adhering and growing on the surface in the absence of cross-linking cannot be released, while the few cells adhering on cross-linked surfaces are released efficiently by pectinase/EDTA. This observation supports the hypothesis that the adhesion and growth obtained with this coating strategy is mainly an effect of the Synthemax II polymer, and that if any PGA is involved it is not in a configuration that promotes protease-free cell release. In FIG. 18, cell release from PGA/Synthemax substrates using pectinase/EDTA is presented in the lower row.

Figure 19A:
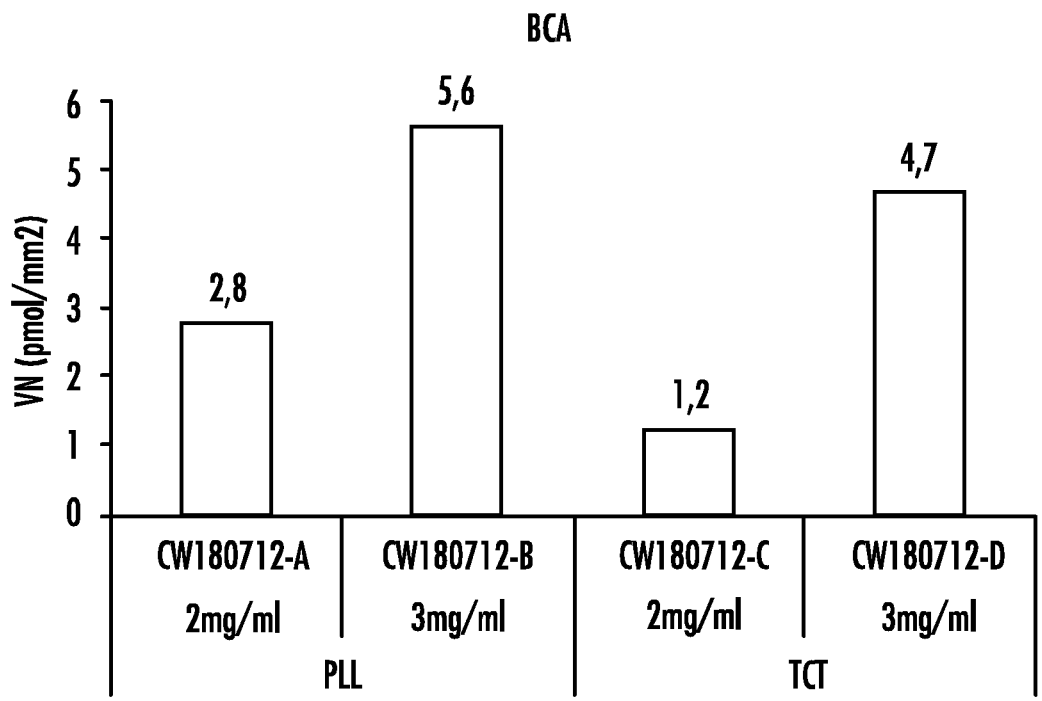
FIG. 19A is BCA results and FIG. 19B is gold staining results for PGA-VN coatings on TCT or PLL substrates for various PGA-VN concentrations.
Figure 19B:
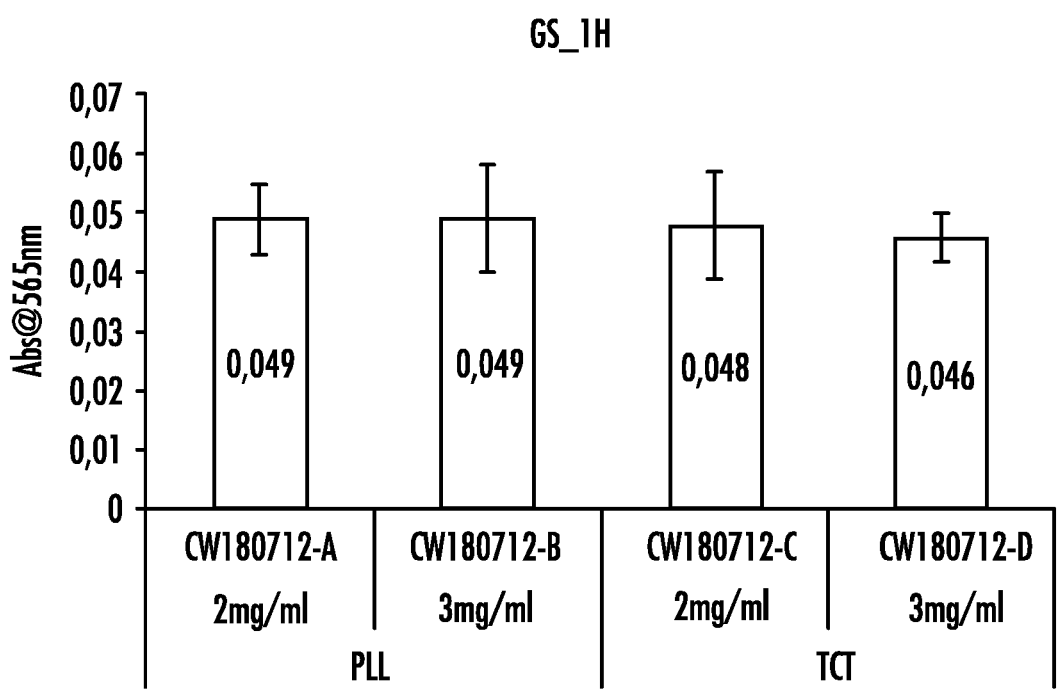

In a further embodiment, a PGA-VN copolymer coating was prepared. TCT or PLL substrates were coated with different concentrations of PGA-VN polymer using the cast and cure method and the polymer was cross-linked with $CaCl_2$ in water. BCA and gold staining results obtained with this approach are shown in FIGS. 19A and 19B respectively.

While there is no apparent impact on the gold staining results, BCA results are slightly better with the PLL substrate and with the higher concentration of 3 mg/ml.

Figure 20:
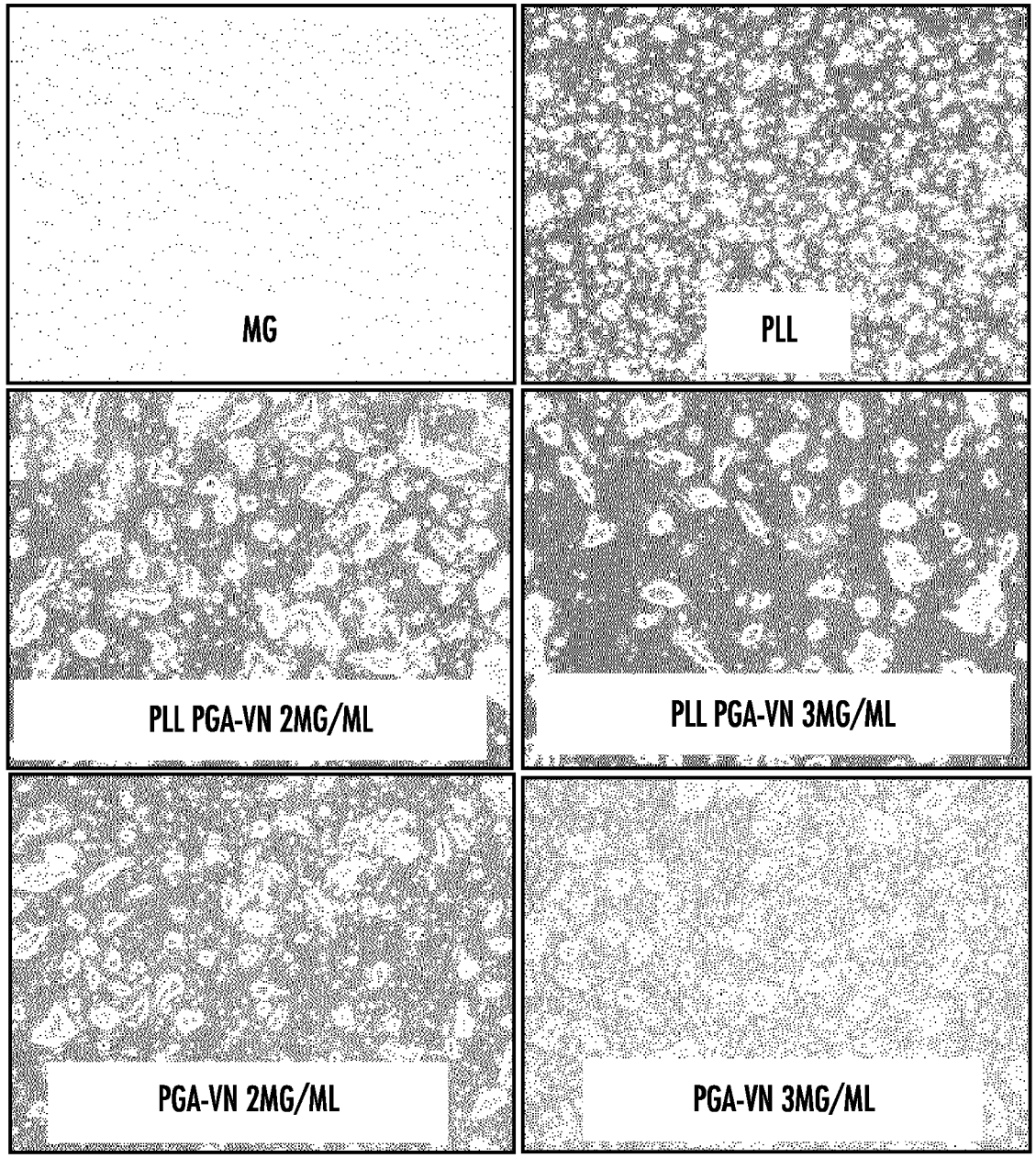
FIG. 20 shows phase contrast micrographs illustrating ES-D3 adhesion on control surfaces and surfaces coated with PGA-VN copolymer.

Results obtained with ES-D3 cells in xeno free medium are presented in FIG. 20, which shows phase contrast micrographs illustrating ES-D3 adhesion at 24 h on controls and surfaces coated with the PGA-VN copolymer. The ES-D3 cells interact with PLL but adhesion and spreading is poor on this surface. Adhesion is better in the presence of the PGA-VN polymer, and the results obtained are slightly better at 3 mg/mL and with a PLL pre-coating.

Figure 21:
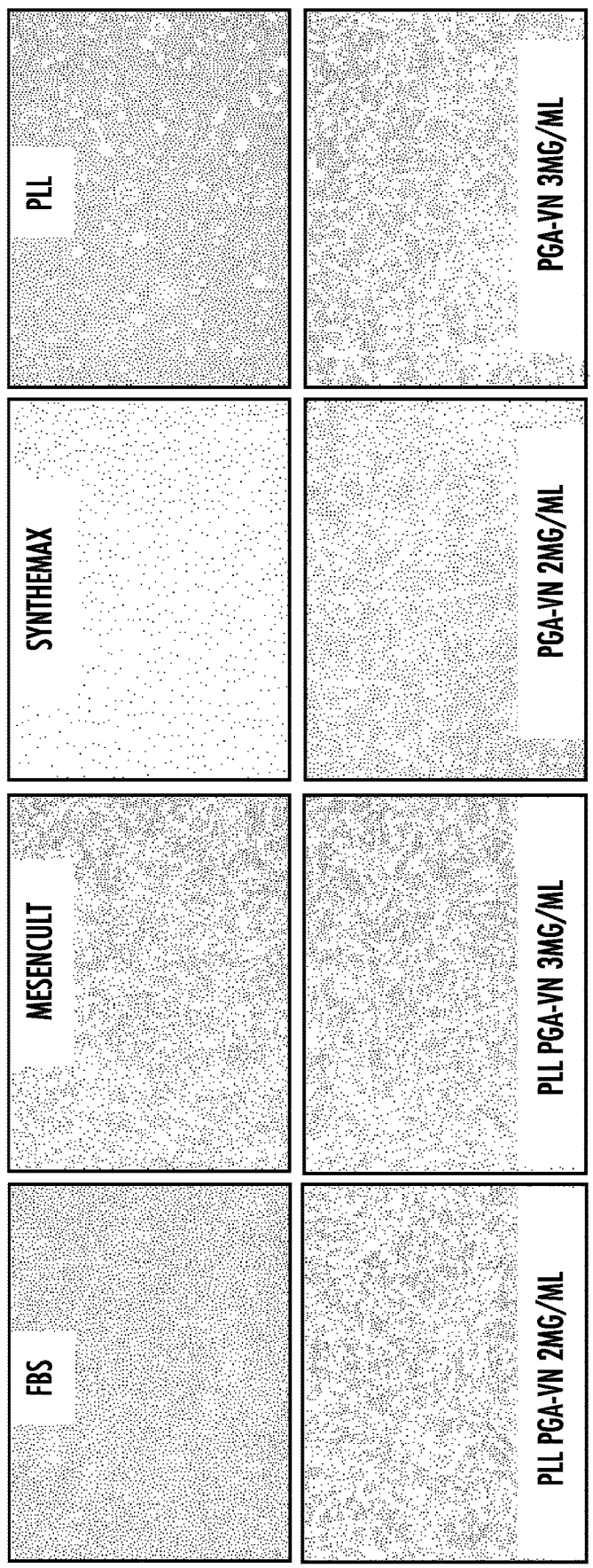
FIG. 21 shows phase contrast micrographs illustrating hMSC adhesion and growth on control surfaces and surfaces coated with PGA-VN copolymer.
Figure 22:
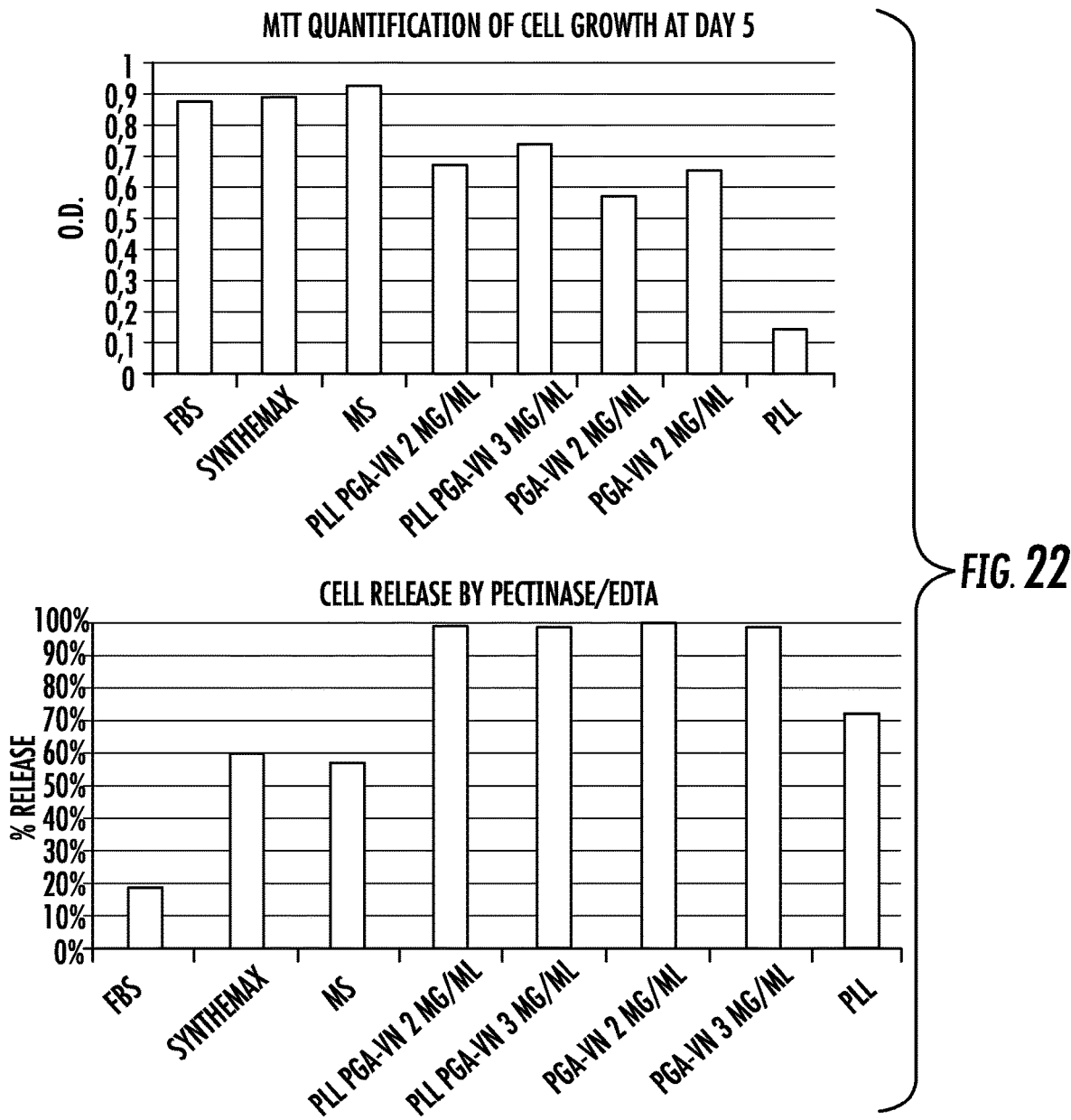
FIG. 22 is quantitative data of cell growth and cell release for hMSC cells on control surfaces and surfaces coated with PGA-VN copolymer.

These plates were then tested with hMSC in mesencult XF xeno-free medium. The phase contrast micrographs in FIG. 21 illustrate adhesion and growth at day 5 on controls and on the PGA-VN copolymer coated plates. Cell repartition is more homogeneous on PLL precoated plates than on TCT plates. Growth on the PLL PGA-VN plates is comparable to what is obtained on Synthemax. Quantification of cell growth and cell release using pectinase EDTA are presented in the histograms of FIG. 22.

Cell quantification using MTT assay indicate that cell growth on PGA-VN is in the 80% range of what is obtained on Synthemax. Complete release is obtained on PGA-VN surfaces after treatment with pectinase/EDTA.

The cast and cure approach provides a decent performance level with hMSC in mesencult-XF, but obtaining a constant coating homogeneity is problematic. In an attempt to improve homogeneity, a coating method using adsorption (KB process) was explored.

Figure 23:
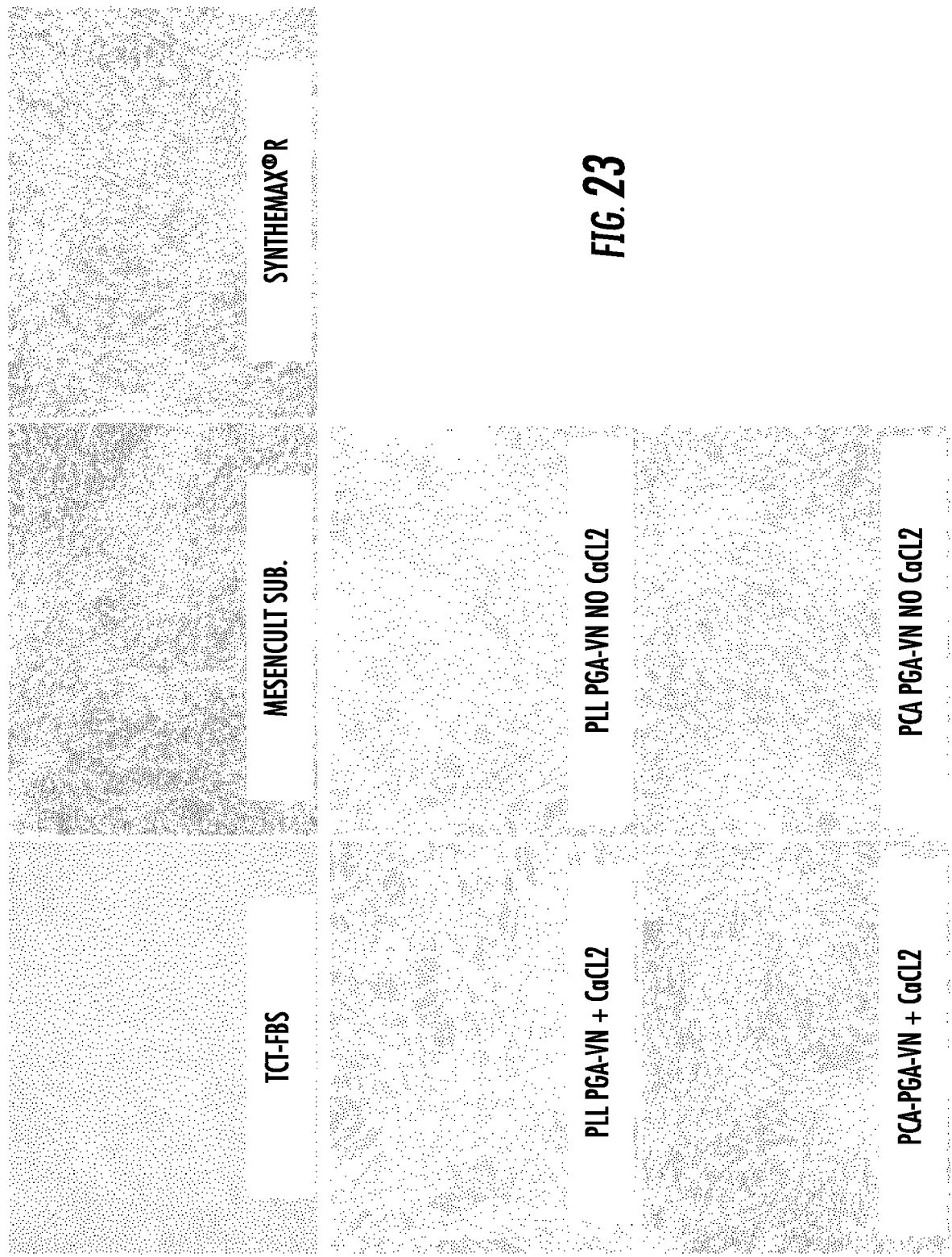
FIG. 23 shows phase contrast micrographs illustrating hMSC adhesion and growth on control surfaces and surfaces coated with the PGA-VN copolymer using a KB process.

The KB process was evaluated on PLL pre-coated plates and on BD PureCoatAmine plates (PCA) with or without $CaCl_2$ crosslinking.

hMSC were grown for 5 days on plates in a mesencult XF medium. Phase contrast micrographs illustrating hMSC adhesion and growth after 5 days on control surfaces and surfaces coated with the PGA-VN copolymer using the KB process after $CaCl_2$ crosslinking or without $CaCl_2$ treatment are shown in FIG. 23. From the data in FIG. 23, the performance level is comparable to Synthemax or mesencult substrates. The coating homogeneity was slightly better on PCA plates than on PLL plates.

Figure 24A:
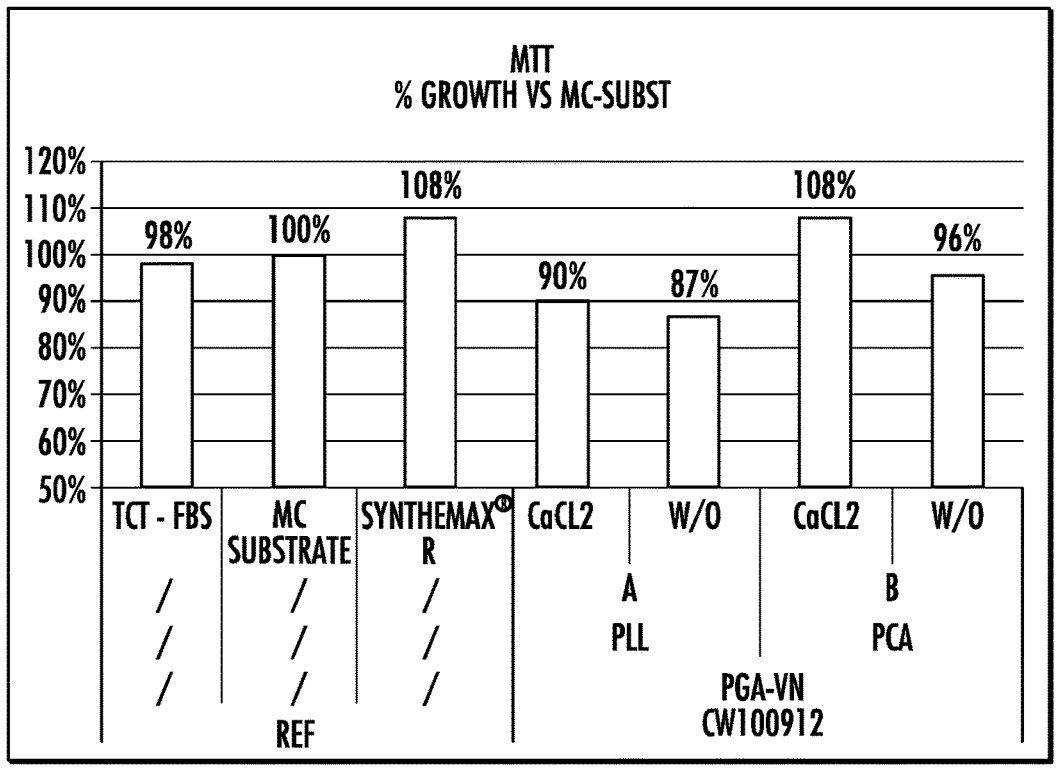
FIG. 24A is quantitative data for hMSC growth at day 5 on Mesencult substrate (MC substrate)
Figure 24B:
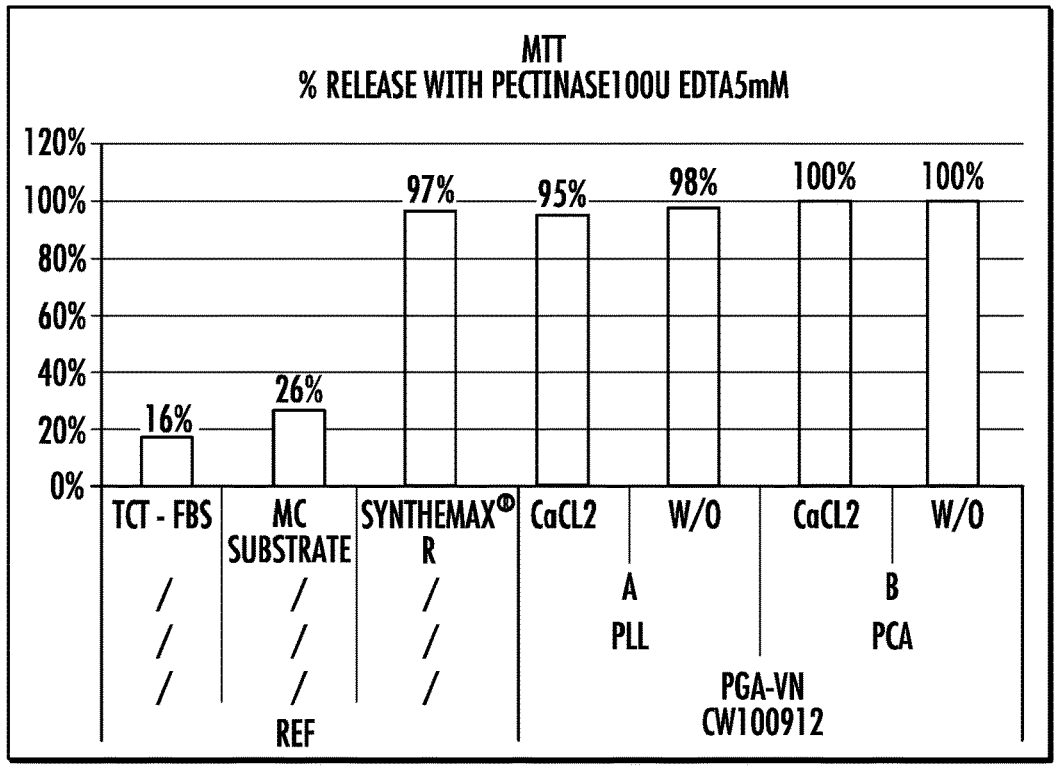
FIG. 24B is cell release data from different surfaces using pectinase EDTA.

MTT cell growth data are summarized in FIG. 24 and confirm that cell growth on PCA PGA-VN is comparable to what is obtained on Synthemax plates. Complete cell release is obtained with pectinase EDTA, but unexpectedly complete cell release is also obtained from Synthemax.

C. Effect of Enzyme/Chelating Agent Concentrations and Treatment Time on Cell Release The impact of pectinase/EDTA concentrations in protease-free cell release protocols from PGA surfaces and non-PGA surfaces was investigated. Also evaluated was release from peptide grafted PGA with pectinase/EDTA in different media, including Mesencult XF, StemGro (Mesen-Gro) and FBS containing media.

Figure 25:
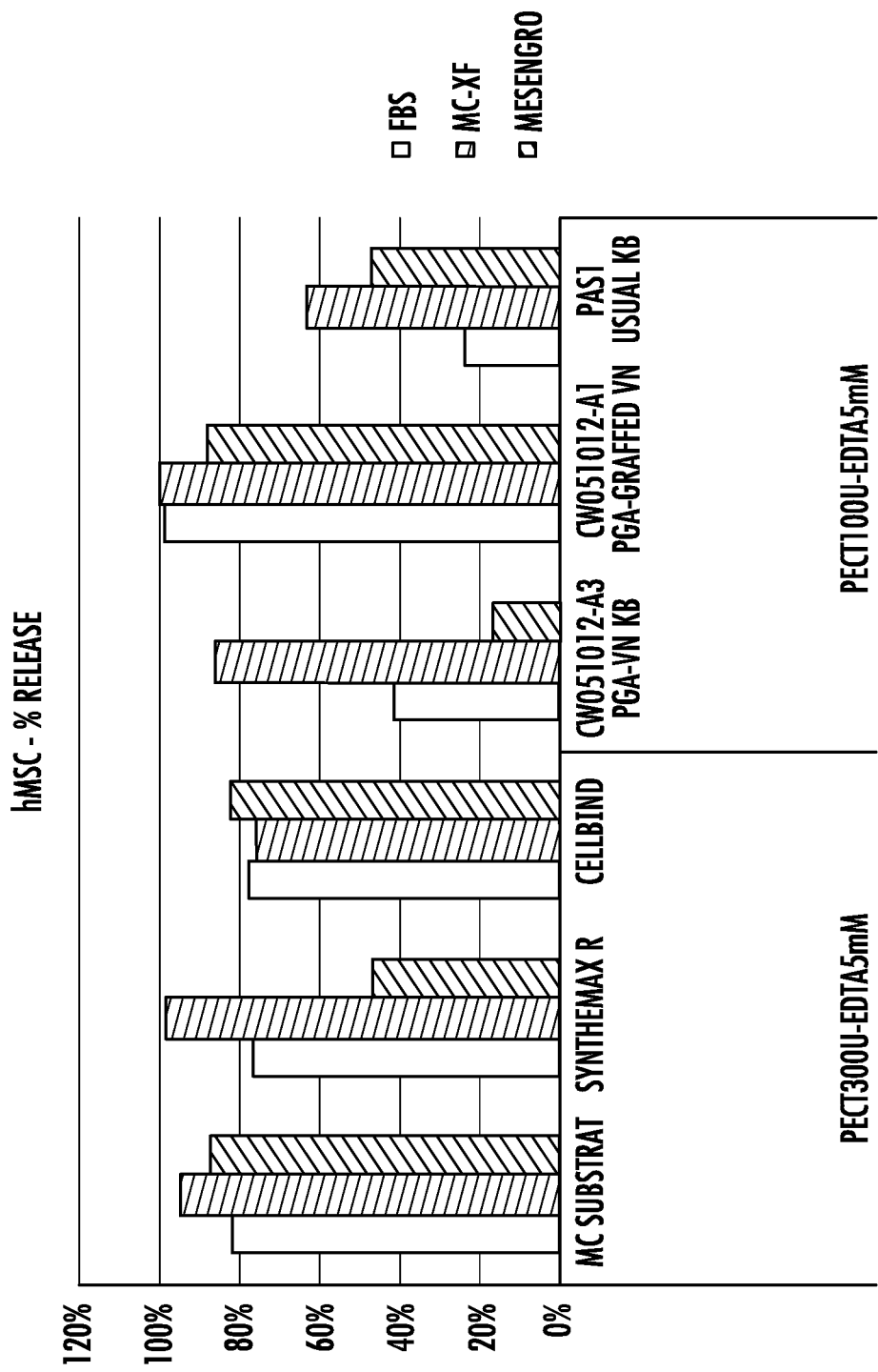
FIG. 25 shows hMSC release data using pectinase/EDTA for various solution concentrations, culture media and surface types.

Data are summarized in FIG. 25. Referring first to the left-hand portion of the graph, a 5 minute treatment with 300 U pectinase/5 mM EDTA induces release of a large proportion of the cells (e.g., at least 70%) under most conditions. The effect of EDTA alone is not sufficient to explain this observation, since no cell release was observed with 5 mM.

The right-hand portion of the FIG. 25 graph, summarizes cell treatment data with 100 U pectinase /5 mM EDTA for KB-PGA-VN, grafted PGA-VN, and Synthemax II (Pas-1 usual KB) surfaces in different media. Interestingly while the release from KB-PGA-VN was only efficient in Mesencult XF medium as previously described, release from grafted PGA-VN was complete, independent of the medium and more rapid than from KB-PGA-VN. With Synthemax II, only partial cell release was observed in the conditions evaluated. These data suggest that depending on conditions, pectinase may induce cell release via two mechanisms: a specific degradation of the PGA polymer as observed with grafted PGA-VN surfaces, and an aspecific mechanism depending on culture conditions as observed on Synthemax II or KB-PGA-VN.

D. Cell Release using Pectinase/EDTA with HEK and MRC5 Cell Lines

Figure 26:
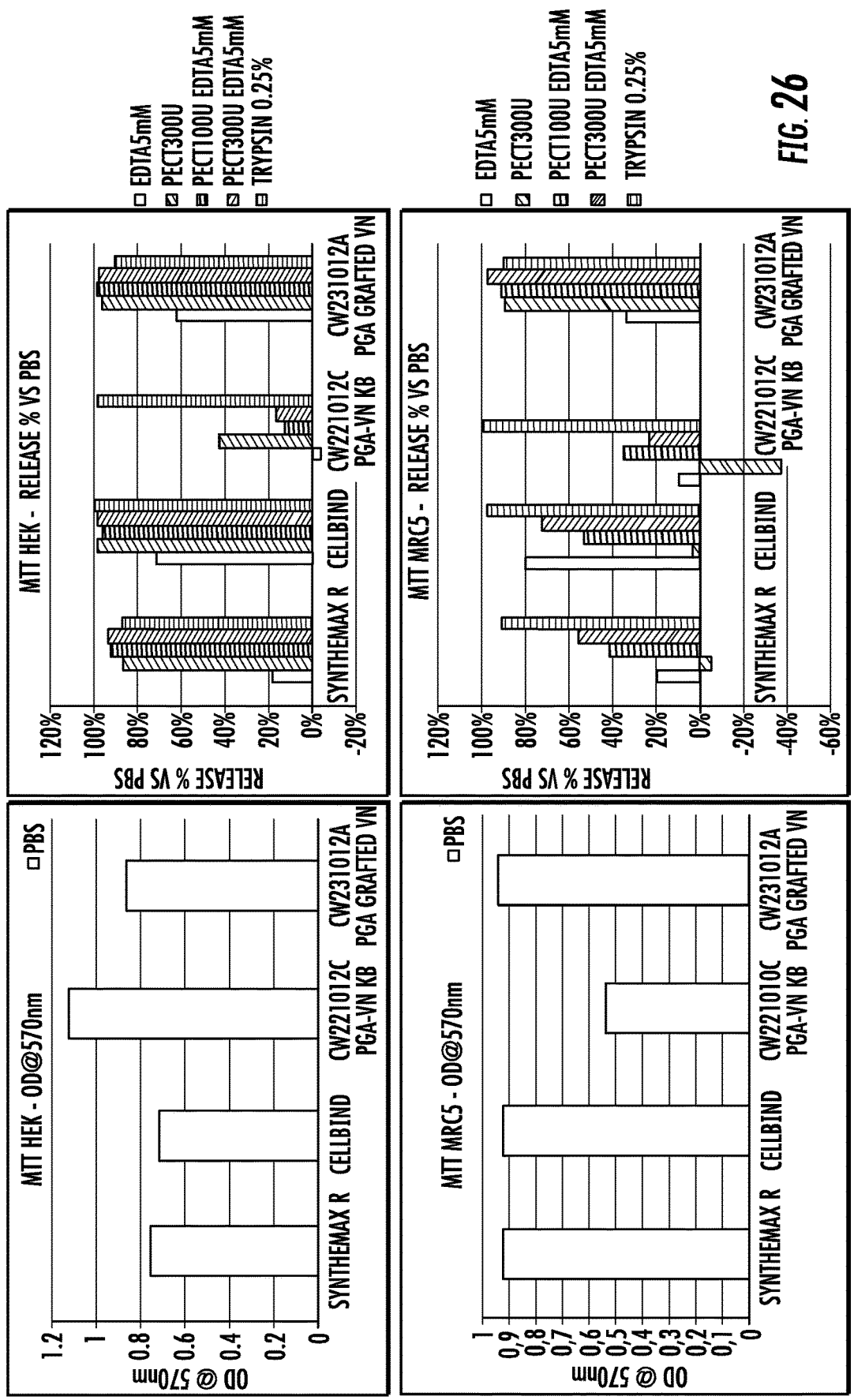
FIG. 26 shows (left) MTT quantification of cell growth at day 5 for HEK and MRCS cells on candidate surfaces, and (right) cell release efficiency for different cell release solutions.

Pectinase/EDTA-induced cell release was evaluated for various surfaces with HEK293 and MRC5 cell lines. Cells were grown for 5 days on Synthemax II, Cellbind, KB-PGA-VN and grafted PGA-VN. Cell growth on these different surfaces was quantified using MTT assays and the results are presented in FIG. 26 (left graphs). As seen with reference to the data in FIG. 26 (right graphs) cell release was then explored using EDTA 5 mM, pectinase alone, pectinase EDTA (100 U/5 mM), pectinase EDTA (300 U/5 mM) or trypsin 0.25%.

As expected, for all cell lines trypsin induces complete release independent of the type of surface. HEK cells release was unexpectedly obtained from Synthemax and Cellbind with all pectinase containing solutions. Release from grafted PGA-VN was expected but the results obtained with other surfaces do not suggest a specific singular mechanism. Interestingly, with KB-PGA-VN no complete release is obtained from KB-PGA-VN plates. This suggests that the release obtained from this surface with hMSC is a least partially aspecific.

With MRC5 cells, as expected, complete release is also obtained from all surfaces with trypsin treatment, but grafted PGA-VN is the only surface from which pectinase-containing solutions are able to induce a complete release. These results indicate that the release obtained from grafted PGA-VN plates involves the degradation of the PGA polymer, but also indicate that pectinase is able to induce cell release with a variable efficiency depending on cell type and culture conditions through a mechanism independent of PGA degradation.

As used herein, the singular forms "a," "an" and "the" include plural referents unless the context clearly dictates otherwise. Thus, for example, reference to a "polymer layer" includes examples having two or more such "polymer layers" unless the context clearly indicates otherwise The term "include" or "includes" means encompassing but not limited to, that is, inclusive and not exclusive.

"Optional" or "optionally" means that the subsequently described event, circumstance, or component, can or cannot occur, and that the description includes instances where the event, circumstance, or component, occurs and instances where it does not.

Ranges can be expressed herein as from "about" one particular value, and/or to "about" another particular value. When such a range is expressed, examples include from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that any particular order be inferred. Any recited single or multiple feature or aspect in any one claim can be combined or permuted with any other recited feature or aspect in any other claim or claims.

It is also noted that recitations herein refer to a component being "configured" or "adapted to" function in a particular way. In this respect, such a component is "configured" or "adapted to" embody a particular property, or function in a particular manner, where such recitations are structural recitations as opposed to recitations of intended use. More specifically, the references herein to the manner in which a component is "configured" or "adapted to" denotes an existing physical condition of the component and, as such, is to be taken as a definite recitation of the structural characteristics of the component.

While various features, elements or steps of particular embodiments may be disclosed using the transitional phrase "comprising," it is to be understood that alternative embodiments, including those that may be described using the transitional phrases "consisting" or "consisting essentially of," are implied. Thus, for example, implied alternative embodiments to a polymer layer comprising PGA and a cross-linking agent include embodiments where a polymer layer consists of PGA and a cross-linking agent and embodiments where a polymer layer consists essentially of PGA and a cross-linking agent.

It will be apparent to those skilled in the art that various modifications and variations can be made to the present inventive technology without departing from the spirit and scope of the disclosure. Since modifications, combinations, sub-combinations and variations of the disclosed embodiments incorporating the spirit and substance of the inventive technology may occur to persons skilled in the art, the inventive technology should be construed to include everything within the scope of the appended claims and their equivalents.

We claim:

1. A method for making an article for culturing cells, comprising:
    forming a polymer coating on a substrate surface, wherein the polymer coating is cross-linked with calcium ions and is at least one selected from the group consisting of polygalacturonic acid (PGA) and alginate and any combination thereof;

forming a cell adhesion layer on the polymer coating, the cell adhesion layer is selected from the group consisting of extracellular matrix (ECM) proteins and synthetic molecules and any combination thereof; and wherein a density of the cell adhesion layer is greater than or equal to 2.5 pmol/mm$^2$.

2. The method according to claim 1, wherein the degree of cross-linking is uniform across the polymer coating thickness.

3. The method according to claim 1, further comprising cross-linking the polymer coating after forming the polymer coating on the substrate.

4. The method according to claim 3, wherein the degree of cross-linking decreases across the polymer coating thickness in the direction of the substrate.

5. The method of claim 1, wherein the polymer coating thickness ranges from 10 nm to 1000 microns.

6. The method of claim 1, wherein the substrate is selected from the group consisting of microcarriers, dishes, bottles, beakers and flasks.

* * * * *